US012797252B2

(12) United States Patent
Fulmes et al.

(10) Patent No.: US 12,797,252 B2
(45) Date of Patent: Nov. 17, 2026

(54) APPARATUS AND METHOD FOR WOUND CARE DEVICE

(71) Applicant: Life Sciences LLC, Easthampton, MA (US)

(72) Inventors: Mychailo Fulmes, Brooklyn, NY (US); Ihor Turkevych, Bradenton, FL (US); Michael McGough, Charlestown, RI (US); Steve Grand, Huntington Beach, CA (US)

( * ) Notice: Subject to any disclaimer, the term of this patent is extended or adjusted under 35 U.S.C. 154(b) by 0 days.

(21) Appl. No.: 18/276,224

(22) PCT Filed: Feb. 7, 2022

(86) PCT No.: PCT/US2022/015423

§ 371 (c)(1),
(2) Date: Aug. 7, 2023

(87) PCT Pub. No.: WO2022/170163

PCT Pub. Date: Aug. 11, 2022

(65) Prior Publication Data

US 2025/0000707 A1 Jan. 2, 2025

Related U.S. Application Data

(60) Provisional application No. 63/146,705, filed on Feb. 7, 2021.

(51) Int. Cl.
*A61F 13/00* (2024.01)
*A61F 13/01* (2024.01)

(52) U.S. Cl.
CPC .. *A61F 13/00063* (2013.01); *A61F 13/01008* (2024.01); *A61F 13/01029* (2024.01); *A61F 2013/0054* (2013.01)

(58) Field of Classification Search
None
See application file for complete search history.

(56) References Cited

U.S. PATENT DOCUMENTS

| | | | |
|---|---|---|---|
| 3,682,180 | A | 8/1972 | McFarlane |
| 3,753,439 | A | 8/1973 | Brugarolas et al. |
| 4,250,882 | A | 2/1981 | Adair |
| 4,553,966 | A | 11/1985 | Korteweg |

(Continued)

FOREIGN PATENT DOCUMENTS

| | | |
|---|---|---|
| EP | 604101 | 12/1993 |
| WO | 2020247571 A1 | 12/2020 |

OTHER PUBLICATIONS

International Search Report and Written Opinion for PCT Application No. PCT/US2014/019519 dated Jun. 3, 2014. 13 pages.

(Continued)

*Primary Examiner* — Kim M Lewis

(57) ABSTRACT

A wound care device may be configured for treating, healing, or monitoring wounds. The wound care device may include a first portion that may be configured to be applied over and external to a wound and a second portion that may be in fluid communication with said first portion that may be configured to be positioned within the wound. The wound care device may wick fluid and other materials from the wound, deliver medicaments to the wound, and supply probes that communicate with displays to show wound status.

14 Claims, 24 Drawing Sheets

(56) References Cited

U.S. PATENT DOCUMENTS

| | | | |
|---|---|---|---|
| 4,815,457 A | 3/1989 | Mazars et al. | |
| 4,917,928 A | 4/1990 | Heinecke | |
| 4,960,467 A | 10/1990 | Peck | |
| 5,053,021 A | 10/1991 | Feibus | |
| 5,078,709 A | 1/1992 | Siciliano | |
| 5,113,871 A | 5/1992 | Viljanto et al. | |
| 5,153,040 A | 10/1992 | Faasse, Jr. | |
| 5,180,375 A | 1/1993 | Feibus | |
| 5,266,371 A | 11/1993 | Sugii et al. | |
| 5,358,492 A | 10/1994 | Feibus | |
| 5,531,999 A | 7/1996 | Cartmell et al. | |
| 5,771,967 A | 6/1998 | Hyman | |
| 5,809,826 A | 9/1998 | Baker, Jr. | |
| 5,840,052 A | 11/1998 | Johns | |
| 5,860,259 A | 1/1999 | Laska | |
| 5,898,964 A | 5/1999 | Stanley | |
| 5,973,221 A | 10/1999 | Collyer et al. | |
| 6,178,984 B1 | 1/2001 | Amsellem | |
| 6,420,622 B1 | 7/2002 | Johnston et al. | |
| 6,432,096 B1 | 8/2002 | McFall et al. | |
| 6,605,068 B2 | 8/2003 | Righetti | |
| 6,884,427 B1 | 4/2005 | Barrows | |
| 6,936,037 B2 | 8/2005 | Bubb et al. | |
| 7,122,712 B2 | 10/2006 | Lutri et al. | |
| 7,182,758 B2 | 2/2007 | McCraw | |
| 7,619,130 B2 | 11/2009 | Nielsen et al. | |
| 7,709,694 B2 | 5/2010 | Batich et al. | |
| 7,790,945 B1 * | 9/2010 | Watson, Jr. | A61M 27/00 604/289 |
| 8,172,818 B2 | 5/2012 | Locke et al. | |
| 9,456,930 B2 | 10/2016 | Zamierowski | |
| 10,085,892 B2 | 10/2018 | Fulmes et al. | |
| 11,311,420 B1 | 4/2022 | Fulmes et al. | |
| 2001/0000796 A1 | 5/2001 | Osborn, III et al. | |
| 2001/0027347 A1 | 10/2001 | Rousseau | |
| 2002/0082540 A1 | 6/2002 | Johnston et al. | |
| 2003/0004579 A1 | 1/2003 | Rousseau et al. | |
| 2003/0068646 A1 | 4/2003 | Singh et al. | |
| 2003/0093075 A1 | 5/2003 | Levinson | |
| 2003/0191442 A1 | 10/2003 | Bewick-Sonntag et al. | |
| 2004/0039415 A1 | 2/2004 | Zamierowski | |
| 2004/0054338 A1 | 3/2004 | Bybordi et al. | |
| 2004/0077103 A1 | 4/2004 | Buechler | |
| 2004/0087980 A1 | 5/2004 | Ford et al. | |
| 2004/0106941 A1 | 6/2004 | Roe et al. | |
| 2004/0249328 A1 | 12/2004 | Linnane et al. | |
| 2004/0262570 A1 | 12/2004 | Radomyselski et al. | |
| 2005/0033251 A1 | 2/2005 | Toreki et al. | |
| 2005/0107731 A1 | 5/2005 | Sessions | |
| 2005/0107756 A1 | 5/2005 | McCraw | |
| 2005/0148920 A1 | 7/2005 | Addison | |
| 2005/0273066 A1 | 12/2005 | Wittmann | |
| 2006/0041247 A1 | 2/2006 | Petrosenko et al. | |
| 2006/0162072 A1 | 7/2006 | Tenenbaum et al. | |
| 2006/0163152 A1 | 7/2006 | Ward et al. | |
| 2006/0241689 A1 | 10/2006 | Leiboff et al. | |
| 2007/0224087 A1 | 9/2007 | Ding | |
| 2007/0265585 A1 | 11/2007 | Joshi et al. | |
| 2008/0132819 A1 | 6/2008 | Radl et al. | |
| 2008/0167593 A1 | 7/2008 | Fleischmann | |
| 2008/0206293 A1 | 8/2008 | Toreki et al. | |
| 2008/0287892 A1 | 11/2008 | Khan et al. | |
| 2009/0025160 A1 | 1/2009 | Ikeda et al. | |
| 2009/0105731 A1 | 4/2009 | Priewe | |
| 2009/0280182 A1 | 11/2009 | Beck et al. | |
| 2009/0313762 A1 | 12/2009 | Boutwell | |
| 2010/0036334 A1 | 2/2010 | Heagle et al. | |
| 2010/0106122 A1 | 4/2010 | Clemens | |
| 2010/0174250 A1 | 7/2010 | Hu et al. | |
| 2010/0210745 A1 | 8/2010 | McDaniel et al. | |
| 2010/0268128 A1 | 10/2010 | Randolph | |
| 2010/0318047 A1 | 12/2010 | Ducker et al. | |
| 2011/0015619 A1 | 1/2011 | Svedman et al. | |
| 2011/0144667 A1 | 6/2011 | Horton et al. | |
| 2011/0208145 A1 | 8/2011 | Zhang et al. | |
| 2011/0240064 A1 | 10/2011 | Wales et al. | |
| 2011/0270201 A1 | 11/2011 | Bubb et al. | |
| 2012/0077886 A1 | 3/2012 | Scholz et al. | |
| 2012/0093759 A1 | 4/2012 | Vachon | |
| 2012/0186016 A1 | 7/2012 | Martin | |
| 2012/0253302 A1 | 10/2012 | Corley | |
| 2013/0035649 A1 | 2/2013 | Locke et al. | |
| 2013/0151223 A1 | 6/2013 | Zamierowski et al. | |
| 2013/0190408 A1 | 7/2013 | Scholz et al. | |
| 2013/0197459 A1 | 8/2013 | Brezoczky et al. | |
| 2013/0217284 A1 | 8/2013 | Wang | |
| 2013/0274629 A1 | 10/2013 | Duesterhoft et al. | |
| 2014/0031735 A1 | 1/2014 | Zurovcik | |
| 2014/0221907 A1 | 8/2014 | Scholz et al. | |
| 2015/0080787 A1 * | 3/2015 | Blott | A61F 13/512 604/27 |
| 2015/0119829 A1 | 4/2015 | Haggstrom et al. | |
| 2015/0157774 A1 | 6/2015 | Zamierowski | |
| 2015/0231314 A1 * | 8/2015 | Robinson | A61M 1/915 604/319 |
| 2016/0256665 A1 | 9/2016 | Doshi et al. | |
| 2016/0270963 A1 | 9/2016 | Zamierowski et al. | |
| 2016/0346444 A1 | 12/2016 | Zamierowski | |
| 2018/0140814 A1 * | 5/2018 | Pratt | A61M 1/92 |
| 2020/0008981 A1 | 1/2020 | Wheldrake | |

OTHER PUBLICATIONS

International Search Report and Written Opinion for PCT Application No. PCT/US2022/015423 dated May 6, 2022. 12 pages.

Braen et al. Manual of Emergency Medicine, 2011, p. 464.

Fulmes et al. "Packing the Closed Incision After Open Colon Resection Can Decrease the Risk of Wound Infection. A Pilot Study," Lehigh Valley Health Network, Department of Surgery, 2012, 3 pages.

Harper. "The Treatment of Injuries to the Soft Parts of the Hand," International Journal of Surgery, vol. 21, Oct. 1908, pp. 303-304.

Today's Wound Care Treatments, Medline, May 2013.

Frederick E. Jackson and Richard A. Pratt. Technical report: A silicone rubber suction drain for drainage of subdural hematomas, Surgery, Oct. 1971: vol. 70, No. 4, 578-579.

Surgical site infections 1: New WHO recommendations on preoperative measures for surgical site infection prevention: an evidence-based global perspective, Benedetta Allegranzi et al. and the WHO Guidelines Development Group, Lancet Infect Dis 2016: Published online Nov. 2, 2016 http://dx.doi.org/10.1016/S1473-3099(16)30398-X.

Surgical site infections 2: New WHO recommendations on intraoperative and postoperative measures for surgical site infection prevention: an evidence-based global perspective, Benedetta Allegranzi et al. and the WHO Guidelines Development Group, Lancet Infect Dis 2016: Published online Nov. 2, 2016 http://dx.doi.org/10.1016/S1473-3099(16)30402-9.

Lee et al. Using a Full-depth Wound Drainage System to Decrease Wound Infection Rates in the Morbidly Obese, Obesity Surgery, 1991, 1: 435-438.

Mcgreal et al. Antiseptic wick: does it reduce the incidence of wound infection following appendectomy, World journal of surgery 26.5 (2002): 631-634.

Claims 1-15 pending at the EPO. EP 22 75 0514. 3 pages.

Extended European search report. Application No. 22750514.6-1102 / 4288008 PCT/US2022015423. Date Oct. 18, 2024. 9 pages.

International Search History for PCT Application No. PCT/US2022/015423 dated May 6, 2022. 12 pages.

* cited by examiner

APPARATUS AND METHOD FOR WOUND CARE DEVICE

REFERENCE TO OTHER APPLICATION

The present application claims priority to PCT/US22/15423, filing date Feb. 7, 2022, entitled "Apparatus and Method for Wound Care Device." PCT/US22/15423 claims priority to U.S. Prov. Pat. App. No. 63/146,705, filing date Feb. 7, 2021, entitled "Apparatus and Method for Wound Care Device." The PCT/US22/15423 and U.S. Prov. Pat. App. No. 63/146,705 are incorporated into the present application in their entirety.

BACKGROUND

The present disclosure relates generally to apparatus and method for wound care device for treating, healing, or monitoring wounds.

Annually, the wound care business is $2.5 billion in the United States of America (USA) and $27 billion globally. The origin of wounds to a body can be internal or external. Wounds of internal origin may be due to impaired circulation, neuropathy, or other medical illness. Wounds of external origin may be from injuries caused by accidents, falls, or hits with blunt or sharp trauma to the body. Furthermore, wounds may be open or closed. In open wounds, the skin is open, and the underlying tissue is exposed to the outside environment. In addition, wounds of external origin may be intentional, such as from a surgical incision produced during various medical procedures.

The USA wastes 3-10 billion dollars annually on wound and post-operative surgical site infection (SSI) expenses. Reducing SSI is a national priority, as reflected in the US Department of Health and Human Services' National Action Plan to Prevent Healthcare Associated Infections. SSI is among the most common health care-associated infections. SSI accounts for up to 30% of health care-associated infections in hospitalized patients and has considerable morbidity with prolonged hospital stays of up to 10 days or more, 3% mortality rate, and average costs of $24,000 per each SSI. Hospitals in the USA are required to report all hospital acquired infections to the Centers for Disease Control and Prevention (CDC), and hospitals with high infection rates have paid an average of over $200,000 per year in fines per facility.

Colorectal surgeries have an acknowledged overall high infection rate of between 15% to 30%. SSI may occur from procedures in specialties including, but not limited to, colorectal, general surgery, OBGYN, urology, vascular, neurosurgery, plastics, and pediatrics. A partial procedure list includes, by way of example and not limitation, abdominal, trauma and many cancer surgeries, stomach and digestive tract, gallbladder, small intestine, large intestine, appendix, liver, pancreas, esophagus, colon, bladder, prostate, uterus, ovaries, kidney, caesarian section, and pediatric. Wounds can be clean, contaminated, contaminated closed incision, etc.

SSI may impact the patient, physician, staff, hospital, insurer, etc. For example, SSI slows the recovery rate for patients and adds additional health costs with prolonged hospital treatment, additional home care, physician office visits, emergency room visits, etc. Patients enduring the traditional old-fashioned healing systems frequently require weeks to recover, extensive follow-up treatments and procedures, and have increased risk of complications including death. Moreover, SSI costs hospitals billions of dollars every year in the USA and insurance companies do not reimburse hospitals for maladies caused by infection, and corresponding complications, due to SSI.

Typically, physicians often respond to the risk of wound infection with the "open wound" technique, subjecting patients to psychological torment of knowing they have an open wound and restricting them from normal activity. The patients are left with a hole in their body that is an open wound that requires additional health maintenance, including additional such as daily dressing changes by visiting nurses, physician consultation, and additional high costs, such as a vacuum device usually for several weeks or longer.

Physicians, attempting to avoid an open wound, will often install a drainage device in the patient. This drainage procedure is accomplished by placing a tube, which may be made of plastic, into the patient, horizontally along the fascia layer and closing the wound around the tube. The most common drains, such as the "J-Drain" and "Penrose Drain", do not remove fluid from all three layers of skin, tend to clog up and can even increase the production of additional fluid in patients, at times making the SSI and recovery issues worse. The drains must then eventually be removed by a surgeon, sometimes weeks after an earlier surgery. Research shows these drains have a poor rate of success with some studies showing an actual increase in patient complications.

Recently, open wound "negative pressure" treatments are now also being touted as the answer for closed incision as well as open wound infection preventative treatments. This treatment simply removes excess fluid from cutaneous areas of the outer skin layer. Furthermore, the negative pressure treatments fail to effectively address the underlining cause of SSI in closed incisions. The negative pressure VAC (vacuum) systems are also very expensive, and physician and nurse-labor intensive. The data regarding the VAC systems appears to be mixed and studies appear to show that these systems involve patients with fewer high-risk factors prior to surgery than may be seen clinical practice.

In addition to the SSI concerns, post-operative surgical wounds can be painful to patients and the pain may require a multimodal treatment plan that may include medicines delivered orally, topically, and injected intravenously, intradermally, subcutaneously, etc. Delivering medicine directly at the site of the surgical wound may help with management of pain in patients and speed up their recovery, which will lower healthcare costs.

Thus, there remains a need for an apparatus and associated method that enables the physician to close the wound without significantly increasing the risk of SSI to the patient, thereby enabling the surgeon to safely close more patients following surgery and improving their lives.

All references cited herein are incorporated herein by reference in their entireties.

SUMMARY

A wound care device for applying within an incision or wound is disclosed.

A wound care device may include a first portion that may be configured to be applied over and external to a wound, said first portion may include a first fluid absorbent material. The wound care device may further include a second portion that may include a second fluid absorbent material, and may have a proximal end and a distal end, wherein the proximal end may be in fluid communication with said first portion, and wherein the distal end may be configured to be positioned within the wound in a subcutaneous skin layer. The wound care device may further include a reservoir operatively coupled to the first portion, wherein the reservoir may be configured to contain a medicament. Said first portion may include a central portion to which said proximal end of said second portion may be coupled, and wherein said first portion may be adapted to form a cover over the wound when said distal end of said second portion may be positioned within the wound. The first fluid absorbent material may have a first fluid-absorbing characteristic and the second fluid absorbent material may have a second fluid-absorbing characteristic different from the first fluid-absorbing characteristic. The first and second fluid absorbent materials may be configured to wick liquids from the second portion to the first portion to facilitate removal of fluid and potentially infectious materials from the subcutaneous skin layer.

Optionally, the wound care device may further include said medicament.

Optionally, the medicament includes a painkiller.

Optionally, the medicament may include at least one of Ketamine, Marcaine and lidocaine.

Optionally, the medicament may include at least one of a Nonsteroidal anti-inflammatory drug, a Corticosteroid, an Opioid, a Muscle relaxant, an Anti-anxiety drug, an antidepressant, and an anticonvulsant.

Optionally, the reservoir may be configured to come into fluid communication with the second portion when a wall of the reservoir may be ruptured.

Optionally, said wall may be configured to act as a divider to thereby prevent said medicament from being in fluid communication with said second portion prior to being ruptured.

Optionally, said divider may be configured to be crumbled or pulverized to provide fluid communication between the reservoir and the second portion.

Optionally, the reservoir may be a holding area in which the second portion may be stored.

Optionally, the wound care device may further include an indicator that may be configured to monitor the wound to thereby detect information relating to the wound.

Optionally, the indicator may be configured to detect temperature.

Optionally, the indicator may be configured to detect pH.

Optionally, the indicator may be provided on the first portion.

Optionally, the indicator may be operatively coupled to a testing strip that may be configured to be placed in the wound.

Optionally, the wound care device may further include a transparent window that may be configured to allow a residue line to be seen therethrough.

Optionally, the first material may include an x-ray detectable material.

Optionally, the second material may include an x-ray detectable material.

Optionally, the x-ray detectable material may include one or more of blue x-ray detectable barium sulfate strands, white x-ray detectable barium sulfate strands, and tungsten filaments.

Optionally, the wound care device may further include a perforation line, wherein the wound care device may be configured to be torn along the perforation line to divide the wound care device into two or more sub-portions.

A method of manufacturing a wound care device for applying within an incision or wound is disclosed.

The method may include providing a first portion that may include a first fluid absorbent material may have a first fluid-absorbing characteristic. The method may further include providing a second portion that may include a second fluid absorbent material may have a second fluid-absorbing characteristic that may be different from the first fluid-absorbing characteristic, the second portion may have a proximal end and a distal end. The method may further include coupling the second portion to a central portion of the first portion such that the proximal end of the second portion may be in fluid communication with said first portion. The method may further include coupling a reservoir to the first portion.

Optionally, the method may further include providing said medicament to said reservoir.

Optionally, the method may further include soaking said second portion in said medicament.

Optionally, the method may further include forming a perforation line in part of the wound care device.

Optionally, the method may further include coupling the second portion to the central portion by stitching.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
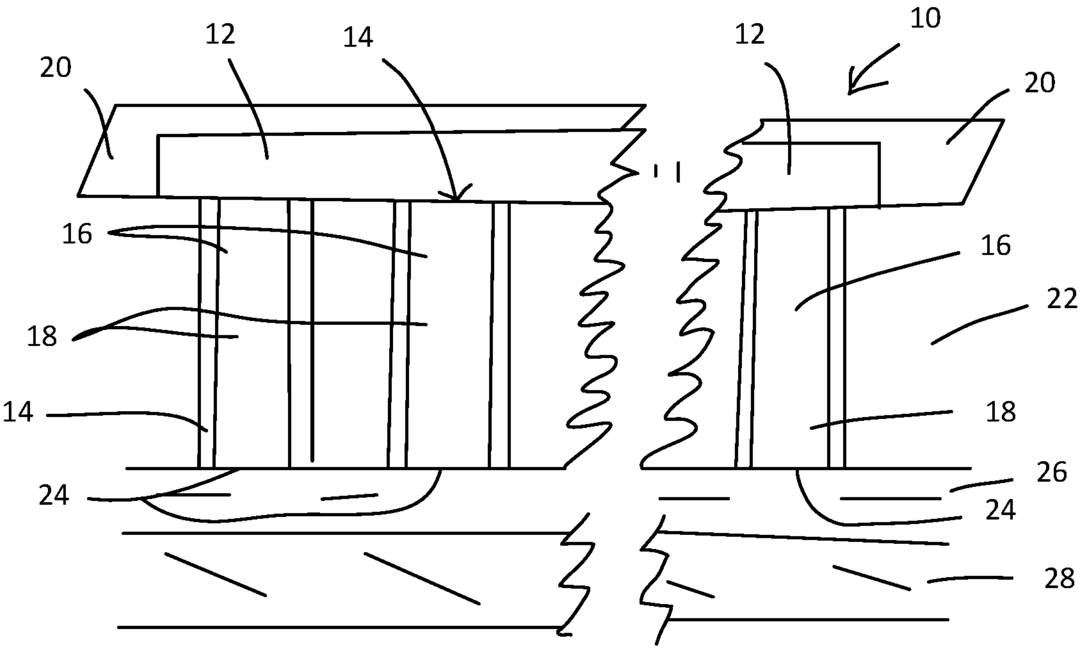
FIG. 1 shows a functional diagram of a wound care device.

Referring now to the figures, wherein like reference numerals represent like parts throughout the several views, exemplary embodiments of the present disclosure will be described in detail. Throughout this description, various parts may be identified having specific values, these values are provided as exemplary embodiments and should not be limiting of various concepts of the present disclosure as many comparable sizes and/or values may be implemented.

A body of a patient may have a wound, and the body may have one or more wounds. The origin of the wounds may be internal or external to the patient. Wounds may include a surgical incision made by a surgeon that is intended to give a surgeon access through skin to underlying tissue in the body of the patent. There is a need for a wound care device that can treat, heal, or monitor the wounds of the patient.

As will also be discussed below, the wound care device may be completely removed from the patient without re-stitching or stapling usually two days following surgery. In some patients, once the wound care device is removed, no other dressings are necessary. In most cases where an additional light dressing is required, the additional light dressing is usually removed within another day or two.

As will be further discussed below, one of the features of the wound care device is that it absorbs fluid and other materials at the source of the fluid and other materials during formation and after the source has formed and the wound care device moves the fluid and other materials out of the body.

The wound care device does not clog, does not involve making additional holes in the patient and exhibits the highest success rate of any infection reduction system on the highest infection risk patients—patients with multiple additional high-risk factors including but not limited to contaminated incision, diabetes, and malnutrition. As will be discussed in detail, the wound care device is a complete fluid absorption system.

FIG. 1 shows a functional diagram of a wound care device (WCD) 10. The WCD 10 may optionally include a first portion 12, which can serve as a dressing over a wound 14. Further, the WCD 10 may optionally include a second portion 16, which can optionally include one or more of a packing strip 18. The packing strip 18 may be configured to be positioned in the wound 14 by a surgeon or other health care attendant (known herein as "surgeon"). The packing strip may extend from a surface 20 of a skin 22 of a patient to a bottom 24 of the wound 14. For example, the bottom 24 of the wound 14 may be at a fascial layer 26, which is above a muscle 28.

The first portion 12 may be referred to as a "dressing." The first portion 12 may optionally include a first fluid absorbing characteristic. The first portion 12 may include any material, either natural or synthetic, or a combination of natural and synthetic materials. For example, but not limited to, the material in the first portion 12 may include cotton, Teflon brand polytetrafluoroethylene, nylon synthetic polymer, packing material, etc. The material in the first portion 12 may have a radiodensity that may be visible on radiography so that material retained in the patient may be detected, so that it may be removed. For example, but not limited to, the material in the first portion 12 may include blue x-ray detectable barium sulfate strands, white x-ray detectable barium sulfate strands, tungsten filaments, etc. In other words, the first portion 12 may be x-ray detectable. The first portion 12 may have a single layer or multi-layered construction or both. The first portion 12 is not limited to a substantially rounded rectangular shape and may optionally assume any shape or size.

The second portion 16 may be referred to as a "packing." The second portion 16 may optionally include a second fluid-absorbing characteristic. The second portion 16 may include any material, either natural or synthetic, or a combination of natural and synthetic materials. For example, but not limited to, the material in the second portion 16 may include cotton, Teflon brand polytetrafluoroethylene, nylon synthetic polymer, packing material, etc. The material in the second portion 16 may have a radiodensity that may be visible on radiography so that material retained in the patient may be detected, so that it may be removed. For example, but not limited to, the material in the second portion 16 may include blue x-ray detectable barium sulfate strands, white x-ray detectable barium sulfate strands, tungsten filaments, etc. In other words, the second portion 16 may be x-ray detectable. The second portion 16 may have a single layer or multi-layered construction or both.

The packing strip 18 may be configured for contacting adjacency with all the layers of the skin 22.

The first fluid-absorbing characteristic of the first portion 12 may be different than the second fluid absorbing characteristic of the second portion 16. The first fluid-absorbing characteristic may be substantially the same as the second fluid-absorbing characteristic of the second portion 16.

The broadest scope of the disclosure includes materials that control the direction of wicking of liquids that may also optionally be used in combination with non-adhering and/or medicated bandage materials.

When the first portion 12 and the second portion 16 are present in the WCD 10, the first portion 12 may optionally be in fluid communication with the second portion 16. Fluid communication between the first portion 12 and the second portion 16 can be achieved in several ways, such as by stitching or via any other method of physically connecting the first portion 12 to the second portion 16, as shown by way of example only and not limitation. Thus, the packing strip 18 may have a surface 20 that may be configured to be adjacent the first portion 12, when present, and the packing strip 18 may have a skin 22 that may be configured to be distant from the first portion 12, when present. The surface 20 of the packing strip 18 may be considered a constrained end or a secured end that may be configured to be adjacent or contactingly adjacent the first portion 12, when present. On the other hand, the skin 22 of the packing strip 18 may be considered a free end or an extreme end that may be configured to be non-adjacent or not contactingly adjacent the first portion 12.

The length of the packing strip 18 of the second portion 16 may optionally by about 2 inches to about 3 inches, although the length of the packing strip 18 could vary to about 4 inches or even about 8 inches or any other dimensions, depending upon size of the patient. The length of the packing strip 18 may be about 5 inches that when manufactured as a loop, as discussed later, may be effectively about 2.5 inches. The length of the packing strip 18 may be about 8 inches that when manufactured as a loop, as discussed later, may be effectively about 4 inches. The length of the packing strip 18 would be selected by the surgeon or other healthcare attendant (herein "surgeon") to be at least equal to the depth of the wound into which the packing strip 18 is placed so that the packing strip 18 reach the bottom of the wound.

Here is an exemplary method of using the WCD 10. The first portion 12 may be positioned on the surface 20 of the skin 22 over the wound 14 of the patient. Transfer of fluid, bodily waste, and infectious materials from the wound 14 to the first portion 12 may be achieved by capillary transfer or any other method of transfer from the second portion 16 in the wound to the first portion 12. One or more of the packing strip 18 of the second portion 16 may be positioned in the wound 14 in an infected area or potentially infected area. The packing strip 18 may facilitate the flow of fluid, bodily waste, and infectious materials from the wound 14 to the first portion 12 outside the skin 22 of the patient.

After surgery on the patient, the wound 14 may be closed by the surgeon using any suitable closure device or method, such as a suture, staple, etc. The wound 14 may be contaminated or clean contaminated or infected. In the wound 14, liquid may accumulate and/or colonize bacteriologically, with the liquid collecting from any and/or all skin layers.

The wound 14 may be closed such that opposing sides of the wound 14 are approximated to be contactingly adjacent via one or more closure device. A surgical covering is placed over the closed wound, such as but not limited to a surgical incision. The surgical covering will be removed so that the WCD 10 may be applied.

The WCD 10 may positioned over the wound 14. The surgeon may manipulate the WCD 10 such that the at least one of the packing strip 18 of the second portion 16 is positioned over the wound 14. The surgeon may further manipulate the WCD 10 in order to properly position the at least one of the packing strip 18 of the second portion 16 in the wound 14. The surgeon seizes the at least one of the packing strip 18 of the second portion 16 with a clamp in preparation to push the packing strip 18 into the wound 14. The surgeon pushes the packing strip 18 through the skin 22 into the wound 14. The process is repeated until all of the packing strip 18 that will be used have been pushed into the wound 14. Typically, the surgeon pushes the packing strip 18 of the second portion 16 down into the in the wound 14 and until the surgeon obtains a tactile indication to stop pushing when the surgeon feels contact with the bottom 24 of the wound 14, which is typically as the fascial layer 26, such that the packing strip 18 is positioned deep into the wound 14. At this point, the surgeon needs only to secure the first portion 12 down onto the surface 20 of the skin 22, which can be done by removing a release liner to expose an adhesive layer, which is optional, from the first portion 12 to releasably secure the first portion 12 to the surface 20 of the skin 22.

The second portion 16 may remain in the wound for approximately 1-3 days at which time they are then removed by the surgeon or other healthcare technician. Fluids that form in the wound are absorbed by the second portion 16 and are drawn upward, out of the wound 14. By removing fluid from the wound 14, the chances for infection are greatly reduced.

The first portion 12 is positioned on the skin 22 directly over the wound 14. The surgeon may have pushed one or more of the at least one of the packing strip 18 into the wound 14.

The WCD 10 may optionally include the first portion 12 that is positioned on top of the skin 22 of the patient over the wound 14. The first portion 12 may be used in combination with non-adhering and/or medicated bandage materials and/or materials that may optionally control the direction of wicking of liquids.

Figure 2:
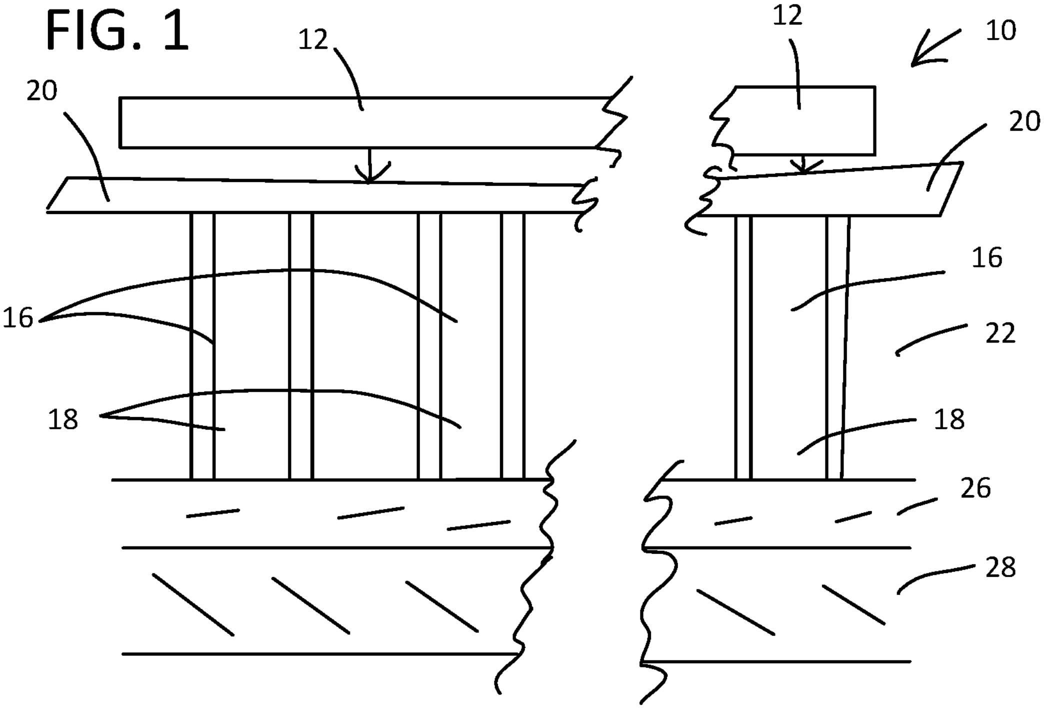
FIG. 2 shows a functional diagram of the wound care device in which the first portion and the second portion are not physically connected.

FIG. 2 shows a functional diagram of the WCD 10 in which the first portion 12 and the second portion 16 are not physically connected. In this configuration, the surgeon may position one or more of the packing strip 18 in the wound 14. Then the surgeon may place the first portion 12 over the packing strip 18 of the second portion 16, such that the first portion 12 and the second portion 16 are in fluid communication. Optionally, the first portion 12 and the second portion 16 may be contactingly adjacent.

The second portion 16 may remain in the wound for approximately 1-3 days at which time the second portion 16 is then removed by the surgeon or other healthcare technician. Fluid and other materials that form in the wound are absorbed by the second portion 16 and are drawn upward out of the wound 14. By removing fluid from the wound 14, the chances for infection are greatly reduced.

It is within the broadest scope of the present disclosure to include the use of all the embodiments of the WCD 10 in open wounds also. By way of example only the WCD 10 is placed inside an open wound, i.e., where no closure devices are used to close the wound 14. Thus, the surgeon places the packing strip 18 of the second portion 16 down into the open wound with the first portion 12 being placed on the surface 20 of the skin 22. Also, by way of example only, the WCD 10 disclosed optionally can be placed also into the open wound and then a separate piece of the first portion 12 may be placed in contact with the packing strip 18 of the second portion 16.

It is within the broadest scope of the WCD 10 to include the conveyance of fluid from the second portion 16 into the first portion 12 by way of the fluid "wicking" across a slight gap between the second portion 16 and the first portion 12. Such an embodiment might be seen in FIG. 2 before the first portion 12 is brought into contacting adjacency with the second portion 16 where fluid absorbed into the second portion 16 might "leap" or "jump" from the second portion 16 through a void that physically separates the second portion 16 from the first portion 12 and such that the fluid is finally absorbed into the first portion 12. Thus, the second portion 16 that is not directly in contact, i.e., not contactingly adjacent, with the first portion 12 is within the broadest scope of the WCD 10.

Figure 3:
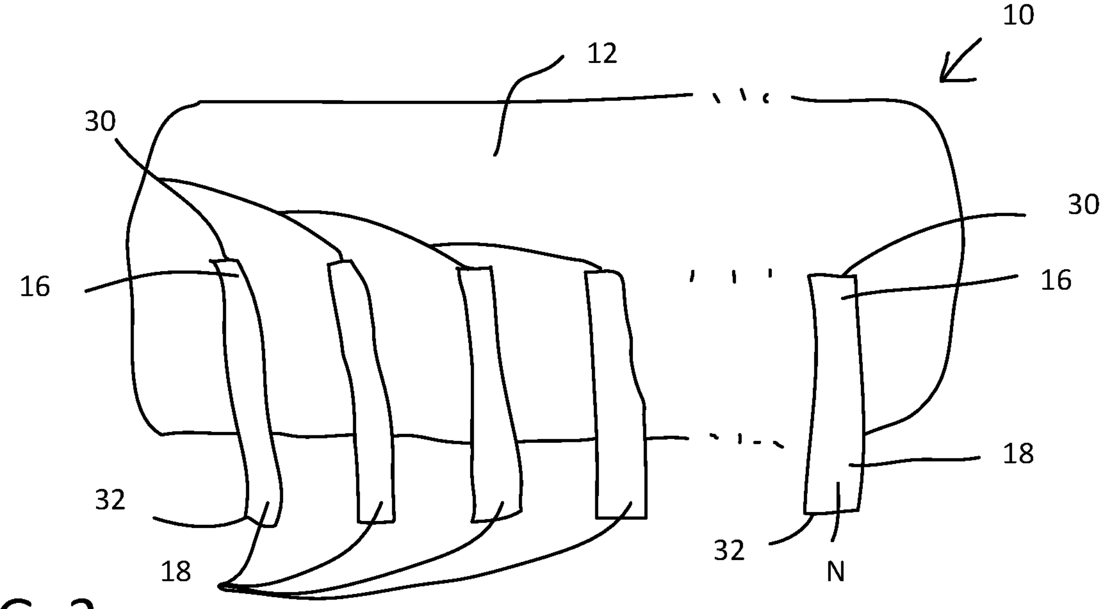
FIG. 3 shows an embodiment of the wound care device in which there are an N number of the packing strip.

FIG. 3 shows an embodiment of the WCD 10 in which there are an N number of the packing strip 18. In this embodiment, each of the N number of the second portion 16 provides one of the packing strip 18. As used herein, N is a number includes all the positive integers from 1 to infinity. Each of the second portion 16 is physically connected to the first portion 12 by a fastener, such as by stitching such as by stitching or via any other method of physically connecting, at a proximal end 30 of the packing strip 18. When the packing strip 18 is fastened to the first portion 12, the proximal end 30 is constrained. A distal end 32 of the packing strip 18 is opposite of proximal end 30. The distal end 32 may be considered a free end that the surgeon can manipulate.

Figure 4:
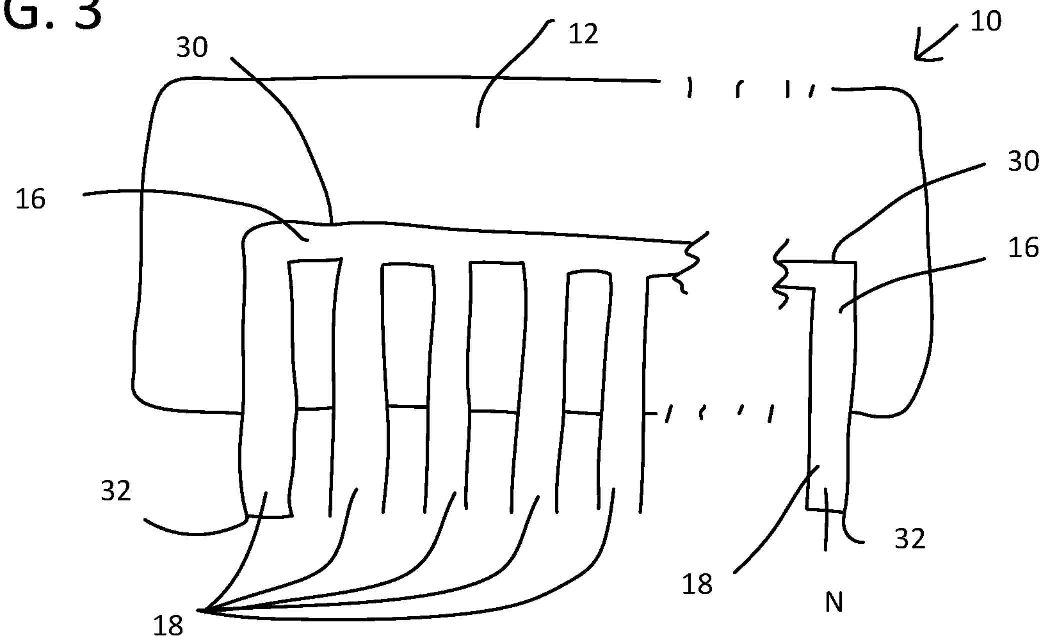
FIG. 4 shows another embodiment of the wound care device in which there are an N number of the packing strip.

FIG. 4 shows an embodiment of the WCD 10 in which there are an N number of the packing strip 18. In this embodiment, the second portion 16 provides the N number of the packing strip 18. Within the broadest scope of the disclosure, each of the second portion 16 may optionally include a tong-like, or comb-like, form to guide or assist the surgeon in placing or positioning the packing strip 18. In other words, there may be one or more the second portion 16 with each of the second portion 16 having one of more the packing strip 18. The second portion 16 of each of the WCD 10 may have different numbers of the packing strip 18. The second portion 16 is physically connected to the first portion 12 by a fastener, such as by stitching such as by stitching or via any other method of physically connecting, towards the proximal end 30 of the packing strip 18. When the second portion 16 is fastened to the first portion 12, the proximal end 30 is constrained. The distal end 32 of the packing strip 18 is opposite of proximal end 30. The distal end 32 may be considered a free end that the surgeon can manipulate.

In another embodiment of the WCD 10 wherein the first portion 12 may optionally include a swath of gauze that can be folded into a multi-layer construction and then closed (e.g., stitched) to reduce the likelihood of the first portion 12 unraveling.

Figure 5:
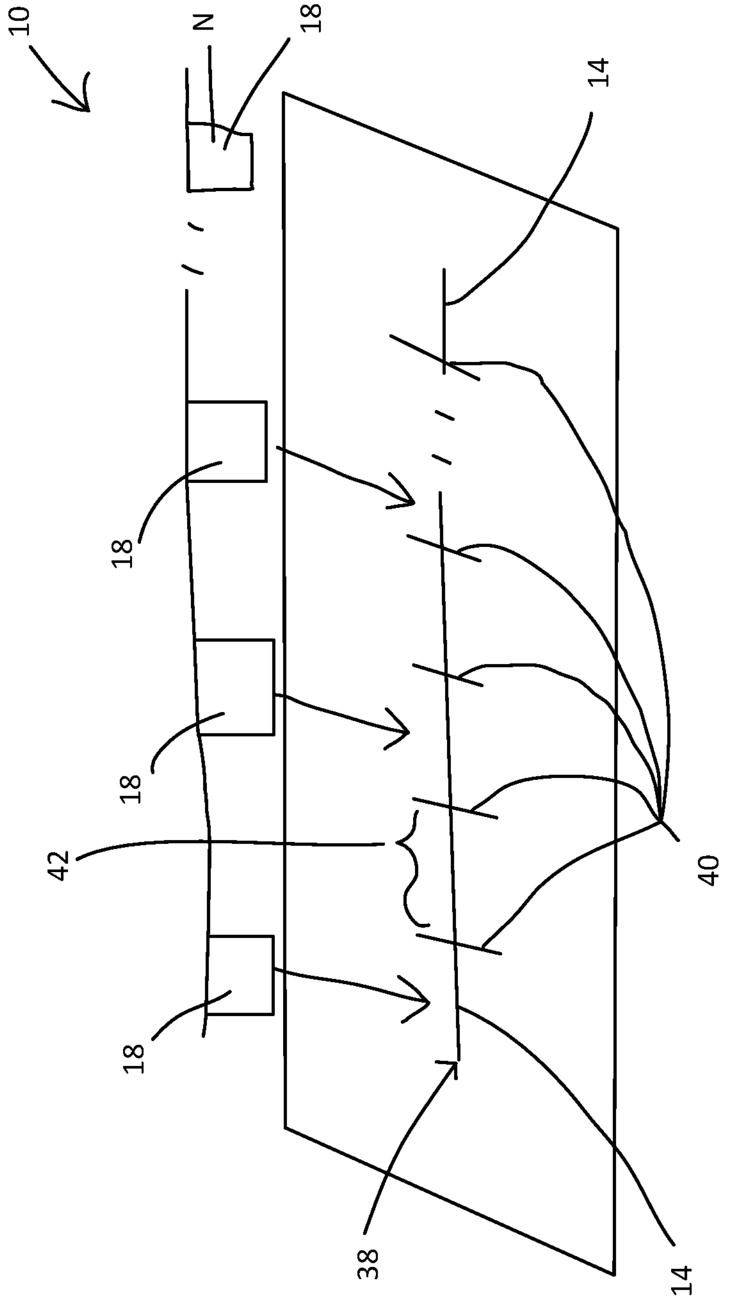
FIG. 5 shows another embodiment of the wound care device in which there are an N number of the packing strip occupying every other space in the wound.

FIG. 5 shows another embodiment of the WCD 10 in which there are an N number of the packing strip 18. The surgeon has positioned the WCD 10 over the wound 14 such that each of the packing strip 18 will be put between a wound end 38 of the wound 14 and a closure device 40 or the packing strip 18 will be placed in the wound 14 between a first of the closure device 40 and a second of the closure device 40, the latter of which can be considered as a closure device interspace 42. In addition, there may be the closure device interspace 42 without the packing strip 18. In other words, it is possible that every other possible space for the packing strip 18 is occupied by one of the packing strip 18 and every other space is not occupied by one of the packing strip 18.

Figure 6:
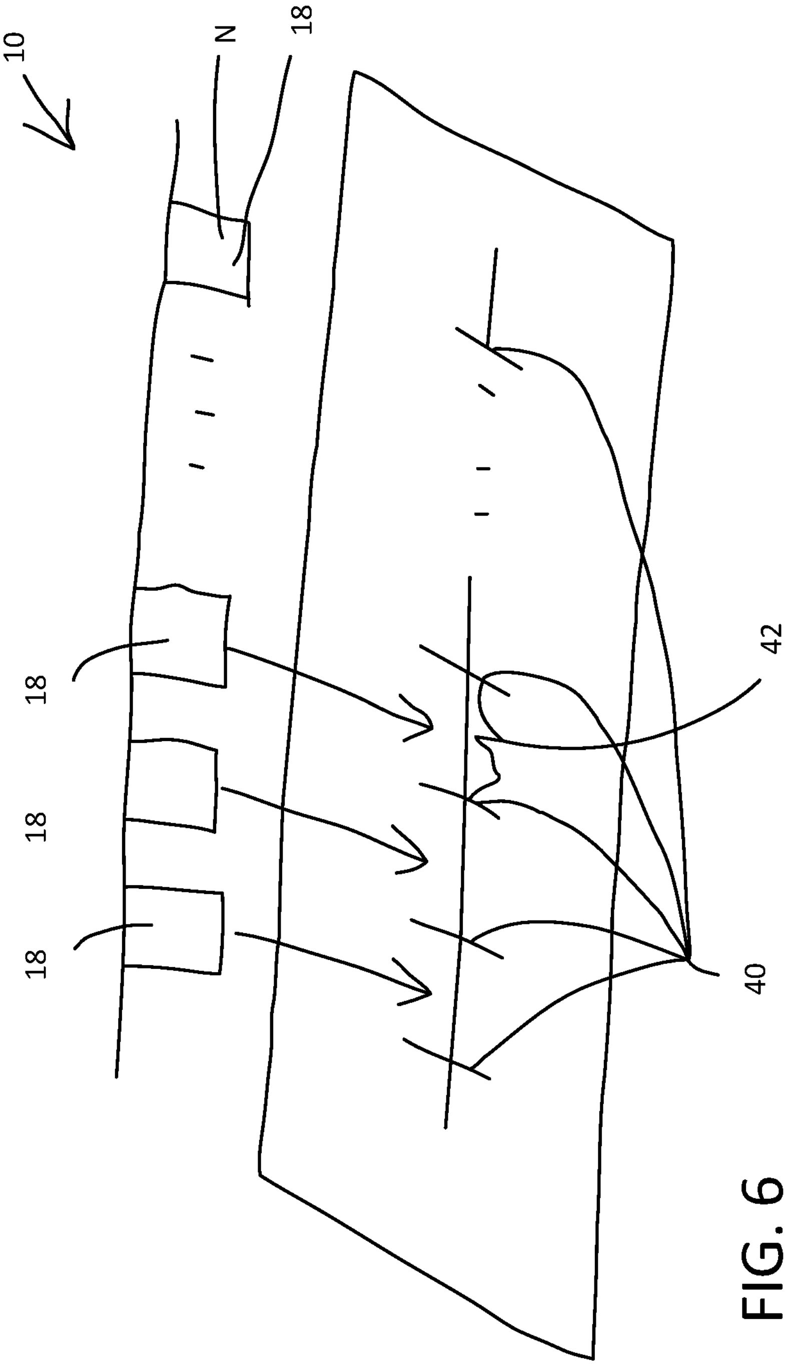
FIG. 6 shows an embodiment of the wound care device with N number of packing strip occupying each closure device interspace.

FIG. 6 shows another embodiment of the WCD 10 with N number of the packing strip 18. In this embodiment, there are enough of the packing strip 18 placed closely enough together on the WCD 10 that immediately adjacent spaces in the wound 14 between the closure device 40 are occupied by the packing strip 18. In other words, the adjacent spaces in the closure device interspace 42 of the wound 14 are occupied by on of the packing strip 18.

Figure 39:
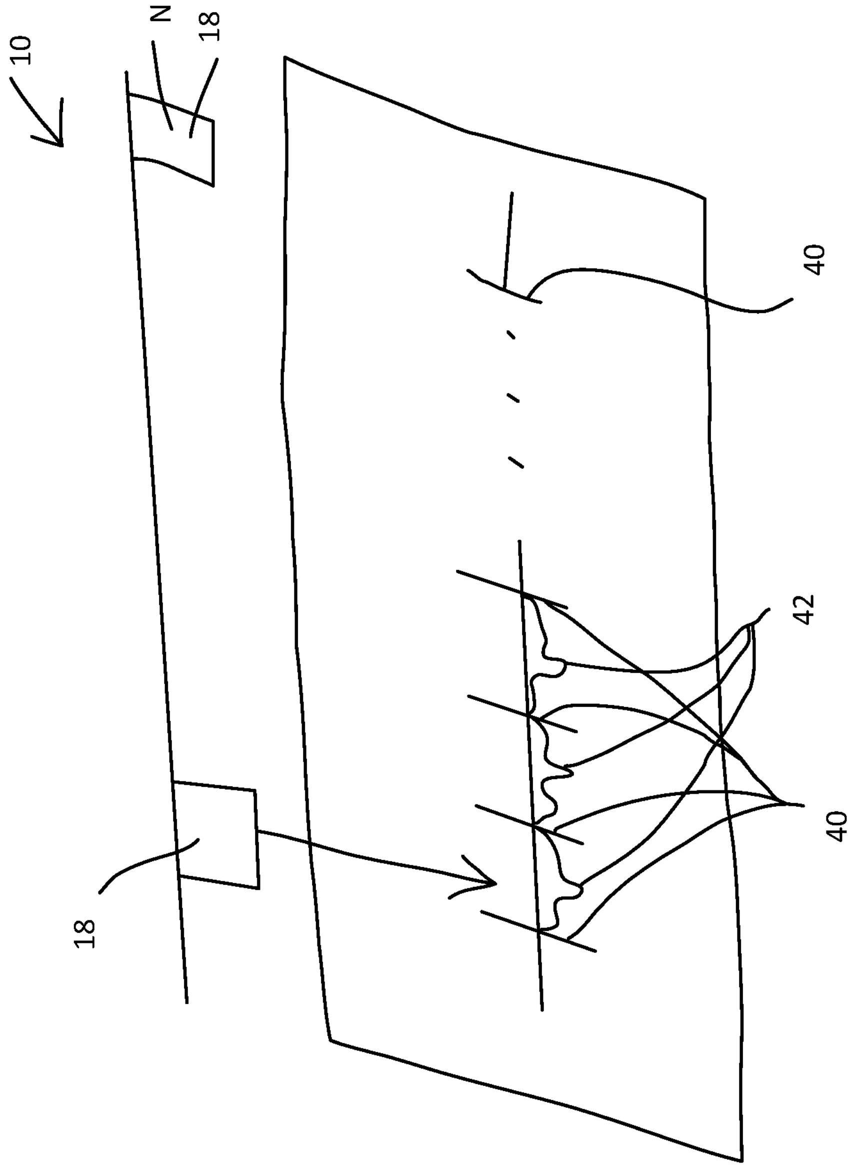
FIG. 39 shows another embodiment of the wound care device with N number of the packing strip.

FIG. 39 shows another embodiment of the WCD 10 with N number of the packing strip 18. In this embodiment, there are few enough of the packing strip 18 placed far enough apart on the WCD 10 that immediately adjacent spaces in the wound 14 between the closure device 40 are not occupied by the packing strip 18. In other words, the adjacent spaces in the closure device interspace 42 of the wound 14 are not occupied by one of the packing strip 18.

Figure 7:
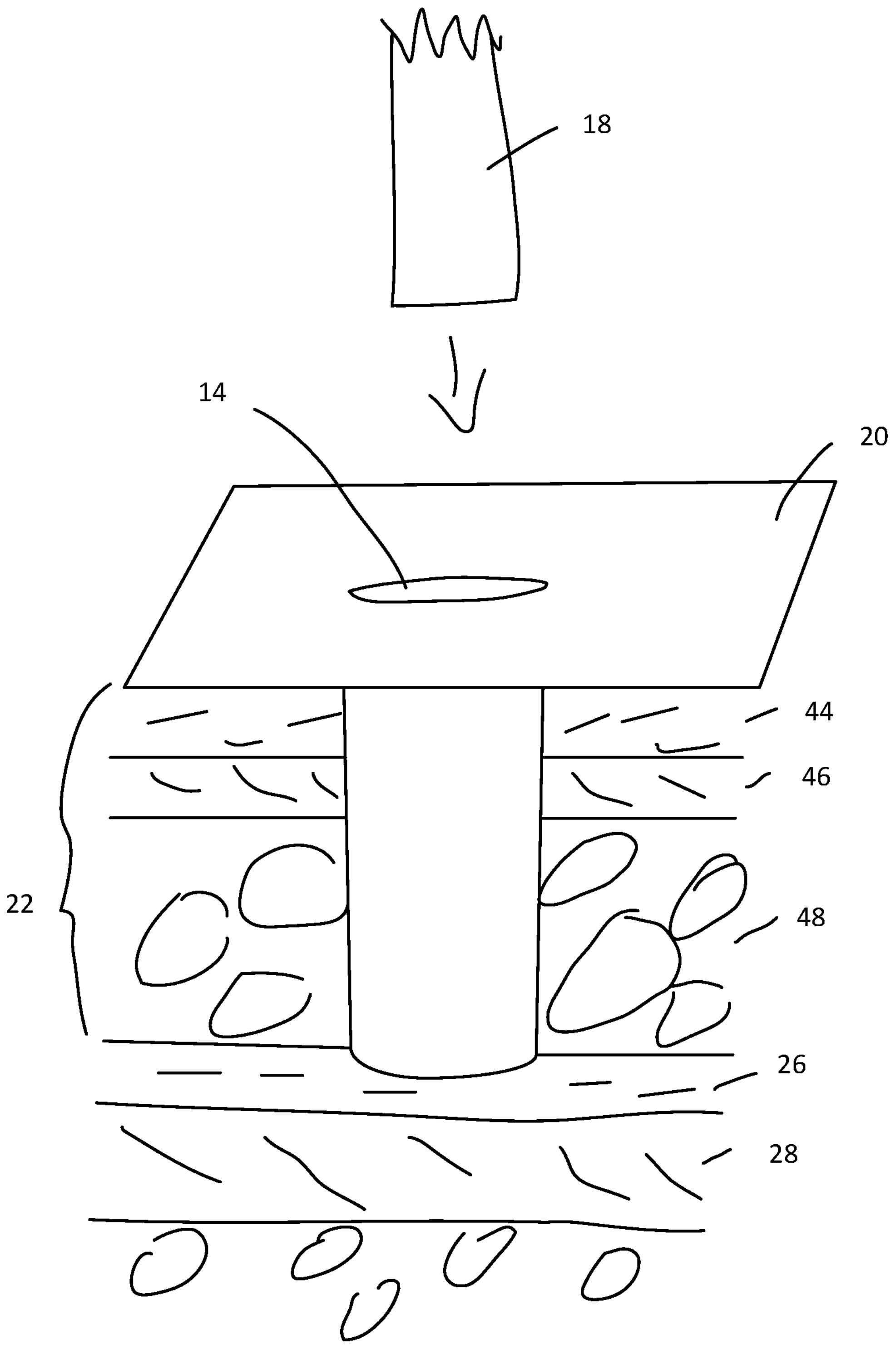
FIG. 7 shows a more detailed embodiment of a method using the packing strip in accordance with various embodiments.

FIG. 7 shows a more detailed embodiment of a method of using the packing strip 18 in accordance with various embodiments. The packing strip 18 is positioned over the wound 14 in the skin 22. The skin 22 may be characterized as having three layers: a, epidermal layer 44 starting at the surface 20, a dermal layer 46 immediately under the epidermal layer 44, and a subcutaneous layer 48 immediately under the dermal layer 46. The epidermal layer 44 and the dermal layer 46 are known collectively as the cutaneous layer. The fascial layer 26 is immediately under the subcutaneous layer 48. The muscle 28 is immediately under the fascial layer 26. Through the packing strip 18 removing fluid and other materials from the epidermal layer 44, the dermal layer 46, the subcutaneous layer 48, and the fascial layer 26, the chances for infection in the wound 14 are greatly reduced.

Figure 8:
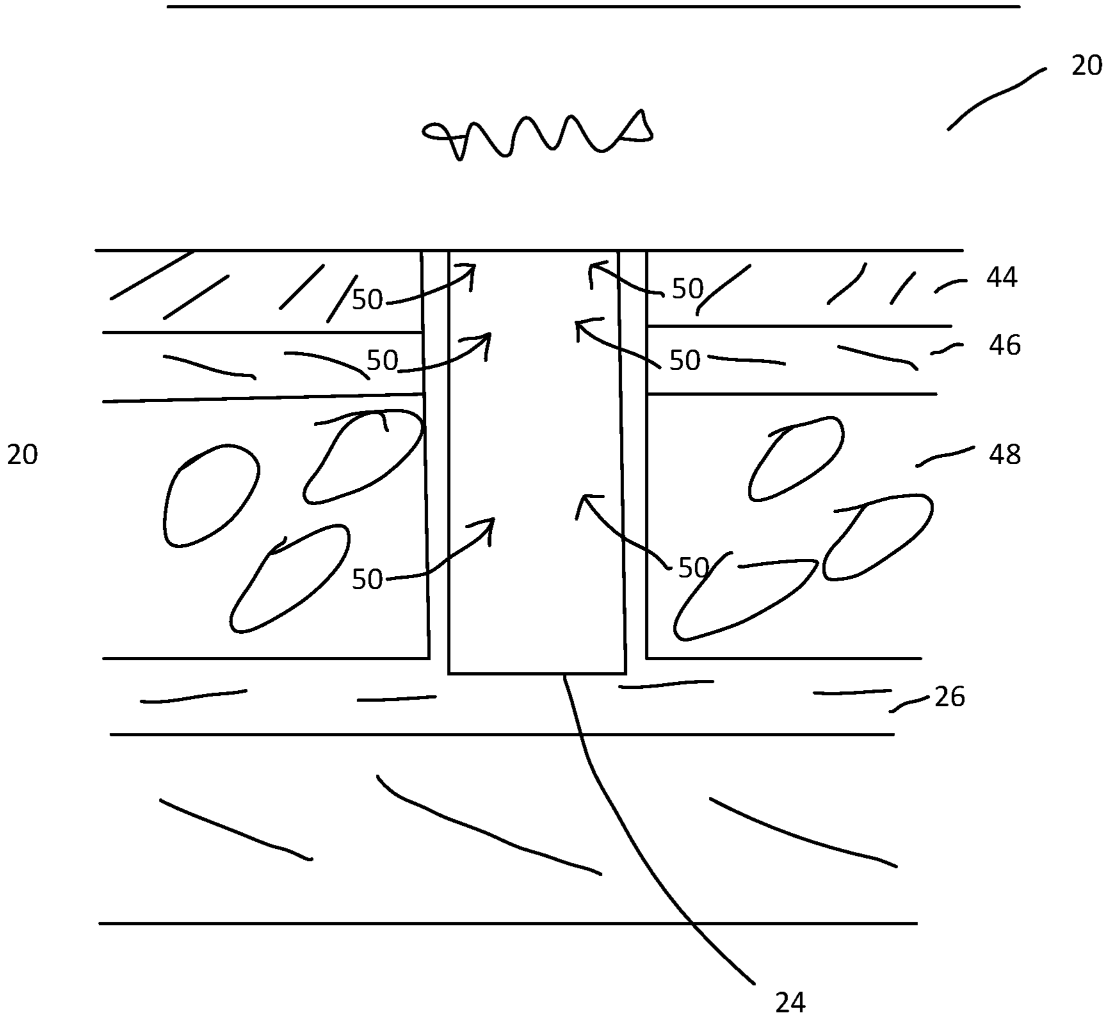
FIG. 8 shows the packing strip positioned in the wound and shows the direction of the wicking action.

FIG. 8 shows the packing strip 18 after being positioned in the wound 14 by the surgeon. The packing strip 18 should be contactingly adjacent to the bottom 24 of the wound 14 at the fascial layer 26 for proper wound care. All three layers of the skin are shown: the epidermal layer 44, the dermal layer 46, and the subcutaneous layer 48. After the wound 14 is formed whether by trauma, by medical illness, surgical incision, etc., there may be production of fluid, bodily waste, or infectious material. By the packing strip 18 being positioned in the wound 14, the fluid, bodily waste, or infectious materials may be wicked out of the wound 14 via the packing strip 18 in the direction as shown by arrow 50.

Figure 9:
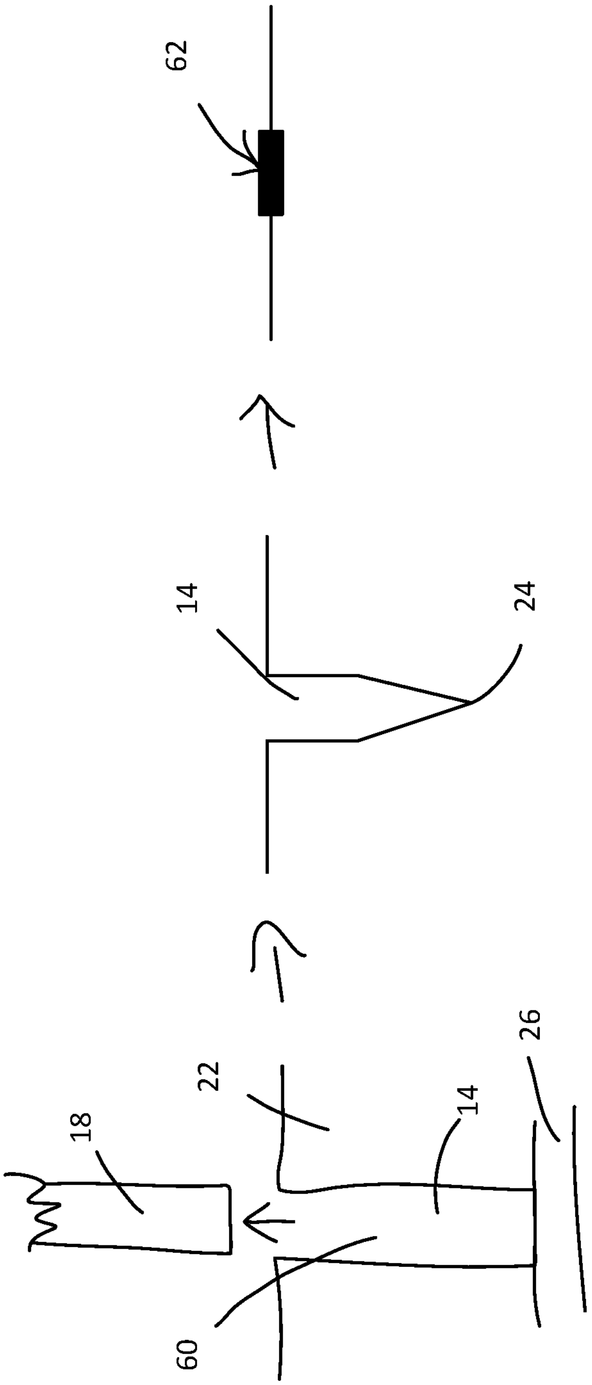
FIG. 9 shows progression of proper healing of the wound after removal of the packing strip.

FIG. 9 shows that after removal of the packing strip 18 from the wound 14, there is a temporary fistula 60 in the skin 22. Over time with proper healing of the wound 14, the wound 14 will close from the bottom 24. And over further time, the wound 14 will close including a scar tissue formation 62 in skin 22. FIG. 9 shows the wound 14 after removal of the packing strip 18 from the wound 14 in approximately 1-3 days after placement, removal of each of the packing strip 18 leaves behind a corresponding one of a temporary fistula 60. The temporary fistula 60 may provide temporary "channels" that permit fluid and other materials in the skin and fascial layer (see FIG. 8) to continue to escape upward of the body of the patient for a finite time after removal of the packing strip 18 and allowing air to enter the wound 14.

Once the packing strip 18 is removed from the wound 14, a conventional bandage (not shown) may be placed over the wound 14. The temporary fistula 60 may continue to drain fluid upward towards the conventional bandage, thereby removing even more fluid and other materials from the skin and fascial layer (see FIG. 8). Eventually, each of the temporary fistula 60 naturally close, from the bottom 24 upward to promote proper healing of the wound 14 after a few additional days (e.g., 1-2 days) following the removal of the packing strip 18. The temporary fistula 60 serves as a natural drainage system that works in conjunction with the patient's normal healing process and the subsequent closure of the temporary fistula 60. The packing strip 18 may be configured to absorb fluid and other materials from all layers of skin 22 and the fascial layer 26 where infection is most common—along the surgical incision.

Figure 10:
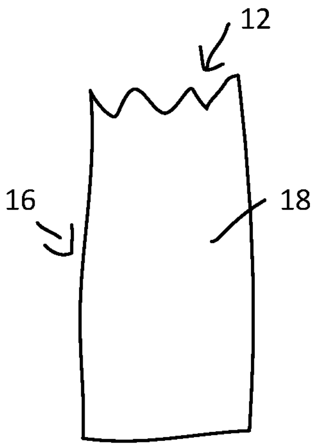
FIG. 10 shows an embodiment of the packing strip in which the packing strip is a single element.

FIG. 10 shows an embodiment of the packing strip 18 of the second portion 16 in which the packing strip 18 is a single element. The packing strip 18 may have any suitable shape, such as but not limited to flat, tubular, etc. Optionally, the packing strip 18 may be in fluid communication with the first portion 12.

Figure 11:
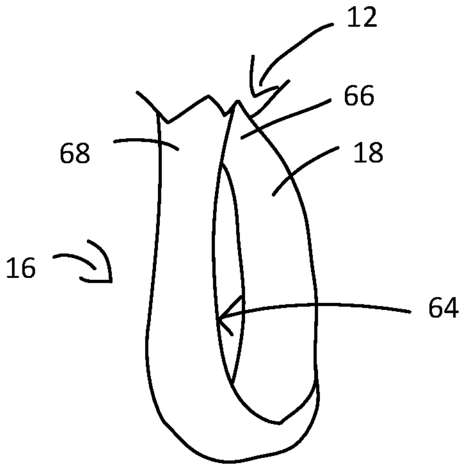
FIG. 11 shows another embodiment of the packing strip in which the packing strip has a loop formed by the packing strip curving back on itself where the packing strip contacts the first portion at each end of the loop.

FIG. 11 shows an embodiment of the packing strip 18 of the second portion 16 in which the packing strip 18 has a loop 64 formed by the packing strip 18 curving back on itself where the packing strip 18 contacts the first portion 12. The surgeon may be able to more easily tell when a loop is broken after use rather than a single element style of the packing strip 18 (see FIG. 10), which may aid the surgeon in determining whether a portion of the packing strip 18 may be left behind in the patient after removal of the packing strip 18 from the patient. A first proximal end 66 of the packing strip 18 is contactingly adjacent a second proximal end of the packing strip 18 at the first portion 12. The first proximal end 66 and the second proximal end 68 are contactingly adjacent the first portion 12.

Figure 12:
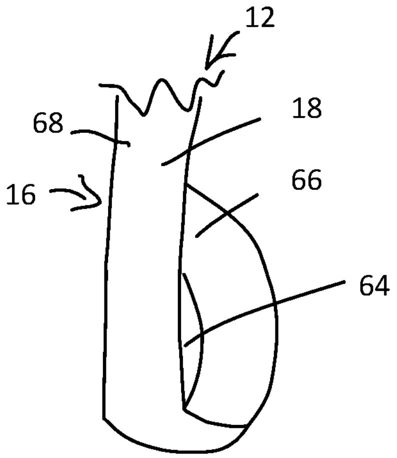
FIG. 12 shows another embodiment of the packing strip in which the loop in the packing strip is closed at a level below the first portion.

FIG. 12 shows an embodiment of the packing strip 18 of the second portion 16 in which the loop 64 of the packing strip 18 is closed at a level below the first portion 12. The first proximal end 66 of the packing strip 18 is contactingly adjacent the second proximal end of the packing strip 18 away from the first portion 12. The first proximal end 66 is contactingly adjacent the first portion 12, and the second proximal end 68 is not contactingly adjacent the first portion 12.

Figure 13:
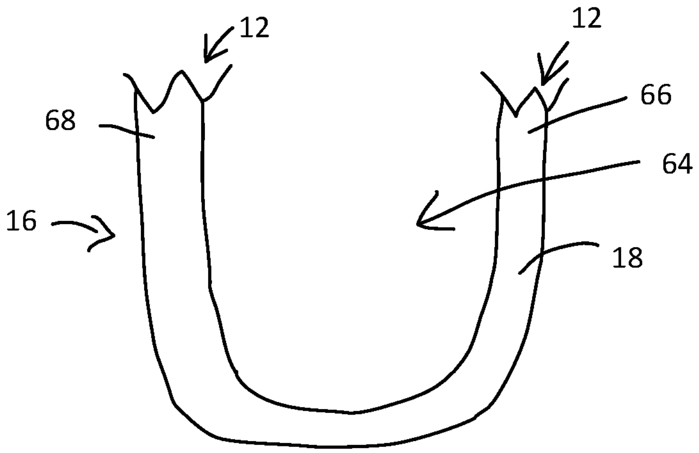
FIG. 13 shows another embodiment of the packing strip with a loop in which the first and second proximal ends of the packing strip are not contactingly adjacent to each other at the contact point on the first portion.

FIG. 13 shows another embodiment of the packing strip 18 of the second portion 16 in which the first proximal end 66 of the packing strip 18 contacts the first portion 12 at a different location not contactingly adjacent the second proximal end 68 of the packing strip 18. The first proximal end 66 is not contactingly adjacent to the second proximal end 68. The loop 64 may be formed by the first proximal end 66, the second proximal end 68, and the first portion 12. The loop 64 may be formed by the first proximal end 66, the second proximal end 68, and the second portion 16. The loop 64 may be formed by the first proximal end 66, the second proximal end 68, the first portion 12, and the second portion 16.

Another improvement to the WCD 10 is the ability to extend length of the at least one of the packing strip 18. This can be advantageous for several reasons. Allowing the surgeon to adjust the length of the at least one of the packing strip 18 permits the surgeon to customize the absorbing capability of the WCD 10 based on the patient's physiology. If, by way of example, the patient has a large girth, it may be necessary to extend the length of the at least second portion 16. However, not all length of packing strip 18 needs to be inside of the patent. Optionally, excess length of the packing strip 18 can be folded as rope on old sailing ships in zigzag form or coiled so it will not knot or tangle. The excess length of the packing strip 18 not needed inside the patient may stay outside the patient under a dressing, for example the first portion 12. In addition, a sleeve outside the patient could be used for this purpose as needed.

Figure 14:
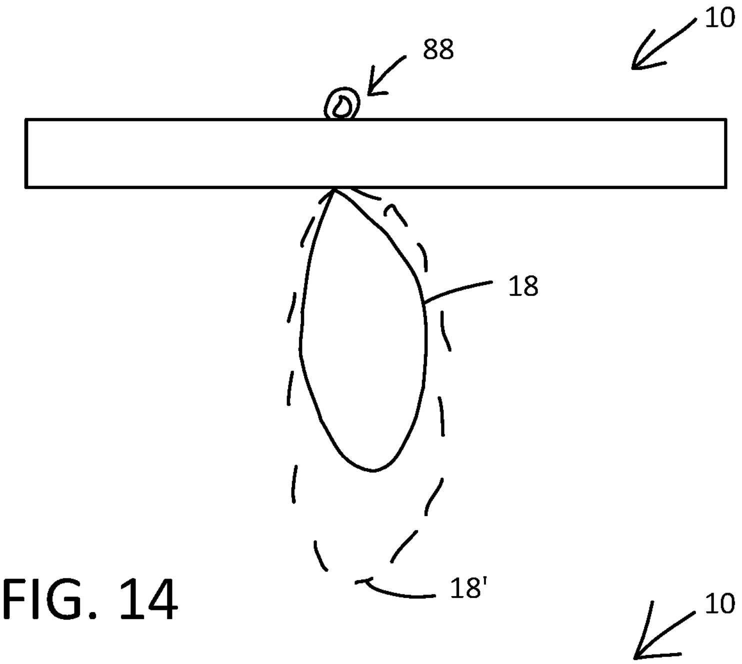
FIG. 14 shows another embodiment of the wound care device wherein respective cartridges of packing strip permit extension of the second portion.

FIG. 14 shows another embodiment of the WCD 10 wherein a cartridge 88 of packing strip 18 permit the packing strip 18 to be extended to new length 18', shown in phantom.

Figure 15:
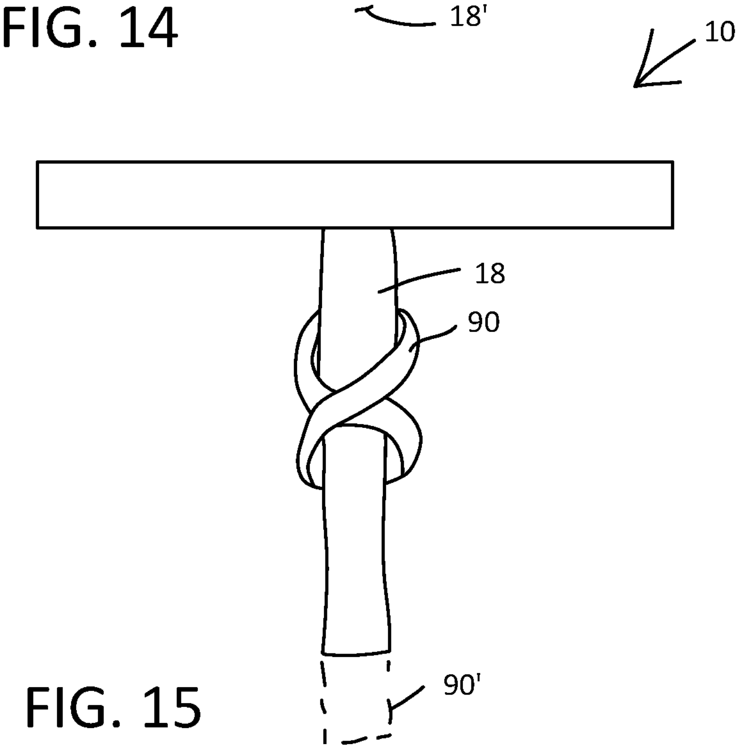
FIG. 15 shows another embodiment of the wound care device that uses a slip knot in each of the packing strip that allows the packing strip to be lengthened.

FIG. 15 shows another embodiment of the WCD 10 that uses a slip knot 90 in the packing strip 18 that allows the packing strip 18 to be lengthened by applying a downward force on the packing strip 18. Excess material formed in the slip knot 90 may permit the packing strip 18 to be lengthened 90'.

Figure 16:
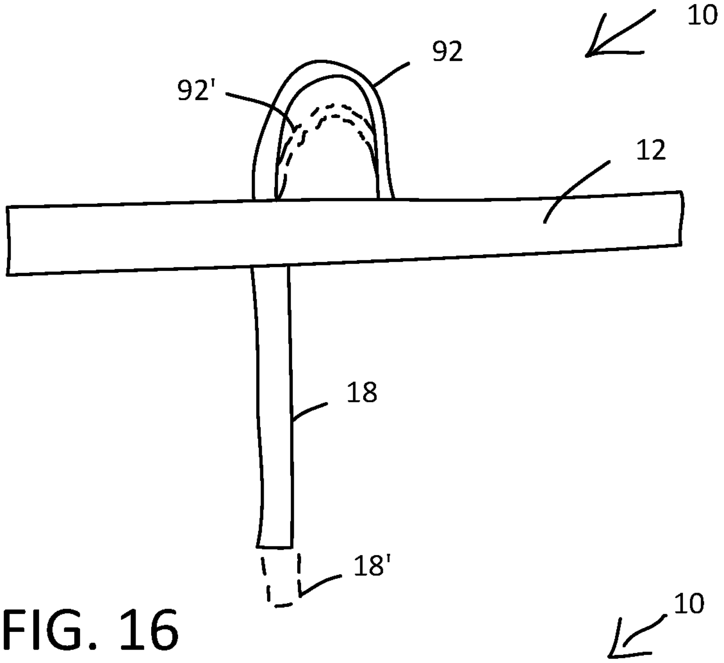
FIG. 16 shows another embodiment of the wound care device where a slack loop that can change length is provided in the first portion.

FIG. 16 shows another embodiment of the WCD 10 in which a slack loop 92 projects from the first portion 12. Thus, when it becomes necessary to extend the length of the packing strip 18, the surgeon can push downward on the packing strip 18 to extend the length of the packing strip 18 to that shown by length 18' by a corresponding decrease 92' in the slack loop 92. The term slack loop in the broadest sense may include rolled or folded or tucked material of the packing strip 18 that are located inside or outside of the first portion 12.

Figure 17:
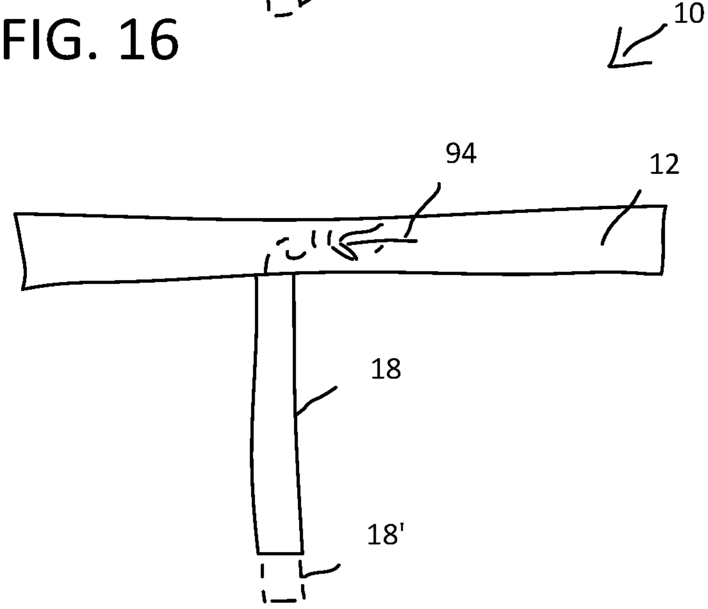
FIG. 17 shows another embodiment of the wound care device where a slack loop projects from the first portion.

FIG. 17 shows another embodiment of the WCD 10 where the slack loop 92 is provided within the first portion 12 itself. An arrow 94 indicates movement as the packing strip 18 is lengthened to that shown by length 18' and the slack loop 92 is shortened. Another approach for variable length of the packing strip 18 would be using a similar principle as a dental floss dispenser, such that that surgeon uses what is needed, from a wheel type dispenser that spins and releases additional length of the packing strip 18.

Figure 18:
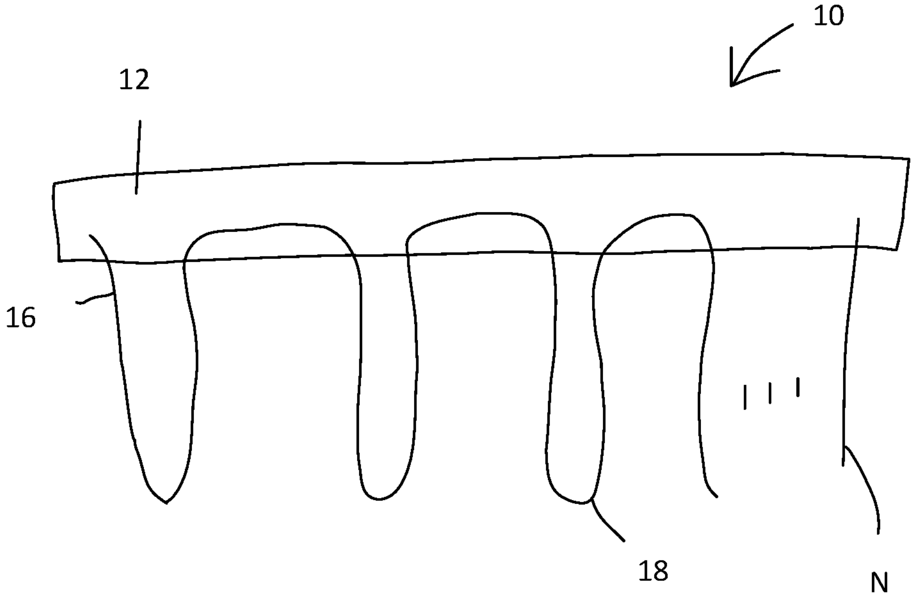
FIG. 18 shows another embodiment of the wound care device where N number of slack loop project from the first portion.

FIG. 18 shows another embodiment of the WCD 10 in which the first portion 12 may be a multi-layer construction and a continuous piece of the second portion 16 runs through the first portion 12 with N number of the packing strip projecting from the first portion 12.

Figure 19:
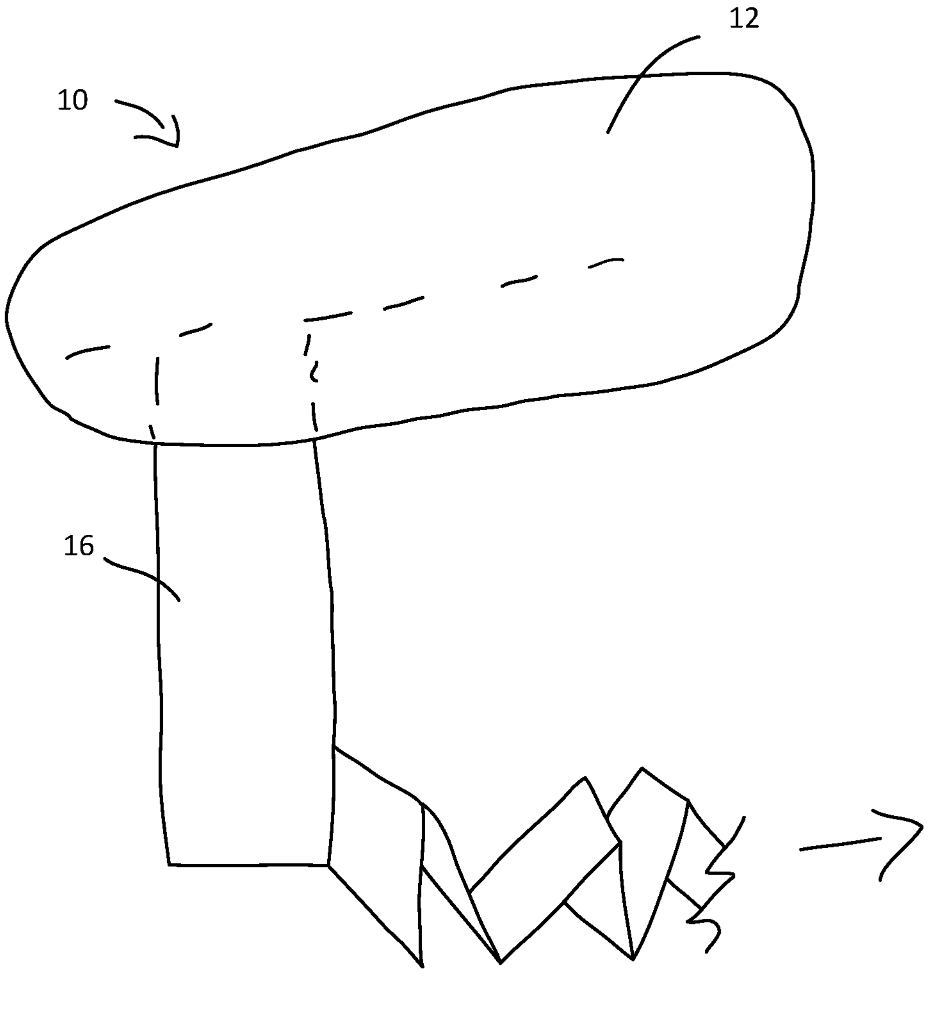
FIG. 19 shows another embodiment of the wound care device wherein the second portion may optionally include a foldable portion that can be expanded outward within the subcutaneous layer or on the fascial layer.

FIG. 19 shows another embodiment of the WCD 10 wherein the second portion 16 may optionally include a foldable portion 100 that can be expanded outward within the subcutaneous layer 48 or on the fascial layer 26 once the second portion 16 is passed into the wound 14. Once the second portion 16 is pushed downward in the wound 14, the surgeon can then expand the foldable portion 100 along the length of the wound 14 within the subcutaneous layer 48 or on the fascial layer 26 (see FIG. 8). The surgeon could then close wound, if necessary.

Figure 20:
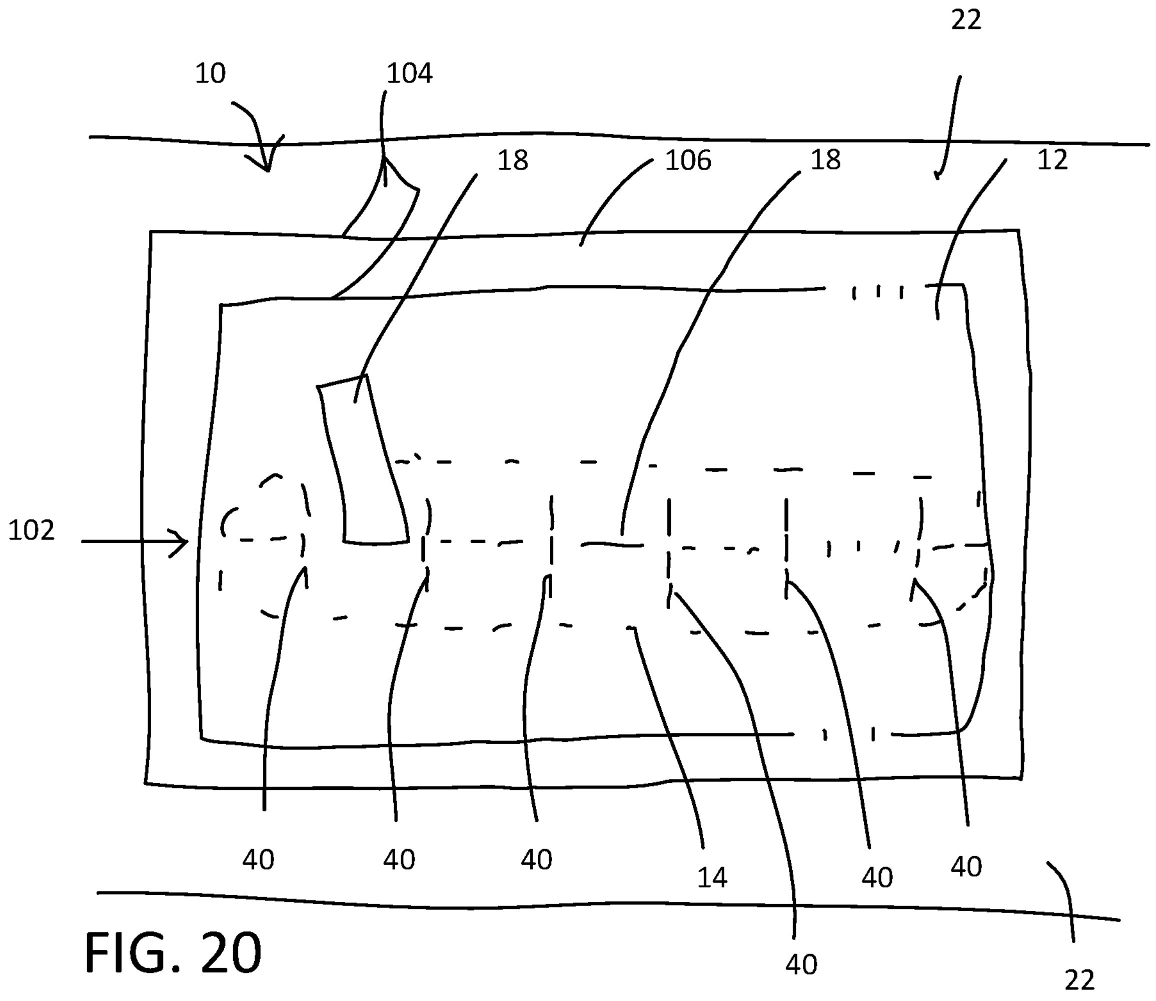
FIG. 20 shows a top view of the wound care device over the wound.

FIG. 20 shows a top view of the WCD 10 over the wound 14. While typically the WCD 10 will be opaque, for this explanation some of the underlying structures are shown. There are N number of the packing strip 18 in the wound 14. Each of the packing strip 18 are oriented in a substantially linear orientation 102. In other words, the WCD 10 has each of the packing strip 18 in a comb-like configuration. This orientation is understandable in that the WCD 10 will often be used on the wound 14 that has had a surgical incision, whether the wound started off as surgery or started because of some trauma. Typically, the surgical incision is substantially linear. In addition, the WCD 10 is shown with a release liner 104 that may be removed by the surgeon to expose an adhesive border 106 that may be used to releasably connect the WCD 10 to the skin 22.

Figure 21:
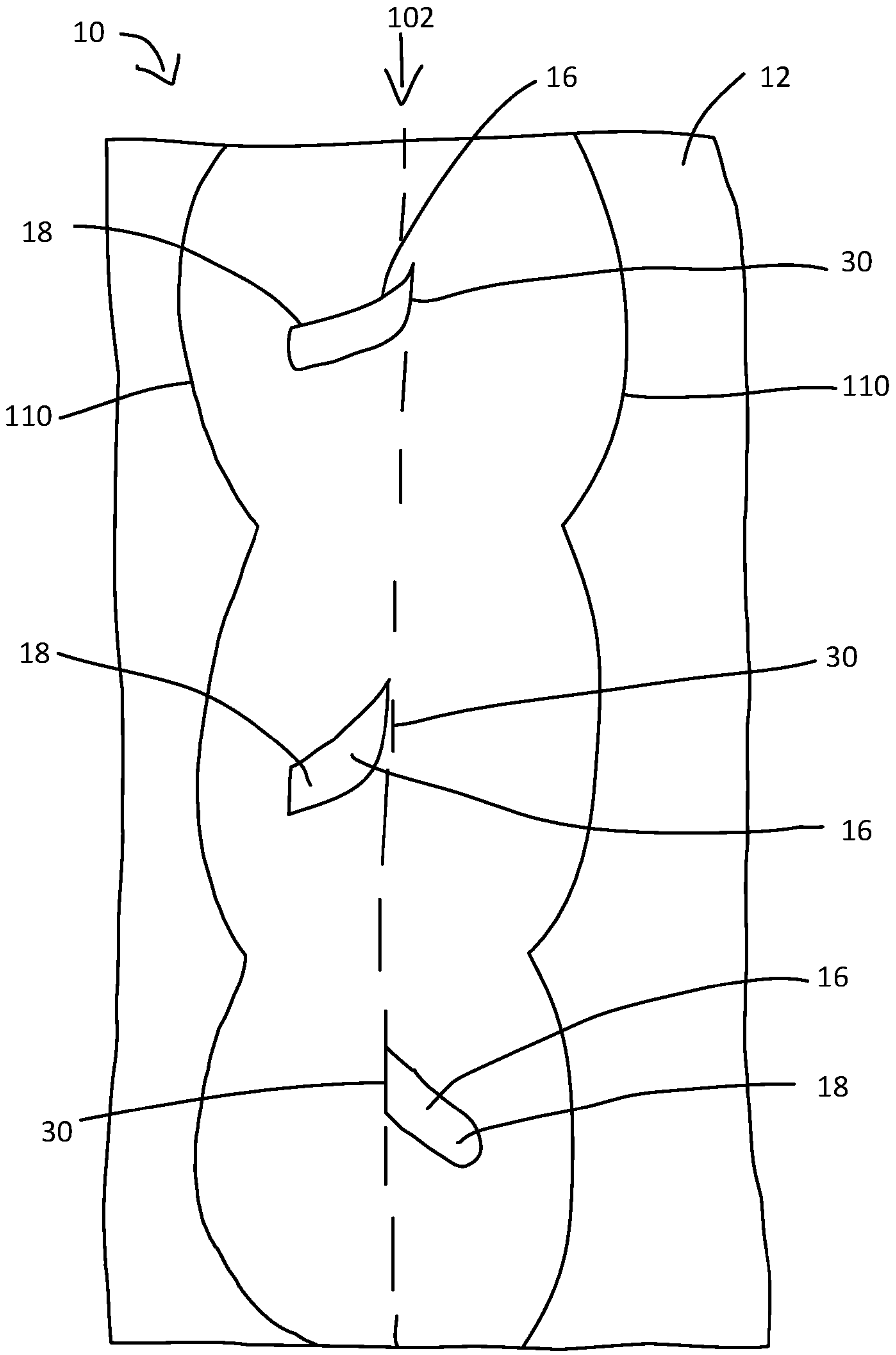
FIG. 21 shows another embodiment of the wound care device with three of the packing strip with residue lines.

FIG. 21 shows an embodiment of the WCD 10 with three of the packing strip 18 of the second portion 16. Of course, more or less than three of the packing strip 18 may be present in the WCD 10. The WCD 10 shown has been removed after usage in the patient. Because the WCD 10 is configured to wick fluid, bodily waste, or infectious material from the body, there may be fluid, bodily waste, or infectious material in the packing strip 18 extending into the first portion 12 away from each of the packing strip 18. There may be a residue line 110 that may be visible or invisible depending on the optical characteristics of the fluid, bodily waste, or infectious material that has been wicked. Each of the packing strip 18 of the second portion 16 are shown connected to the first portion 12 at the proximal end 30 in the substantially linear orientation 102. Because the second portion 16 in this embodiment are widely spaced or distributed, the residue line 110 may have a curvilinear appearance. Of course, the second portion 16 shown as in FIG. 23 may be of any type of the second portion 16 and packing strip 18 disclosed in the present application. How far the fluid and other materials flow into the first portion 12 will, of course, depend on the viscosity of the fluid, type of material present, etc. that has been wicked.

Figure 22:
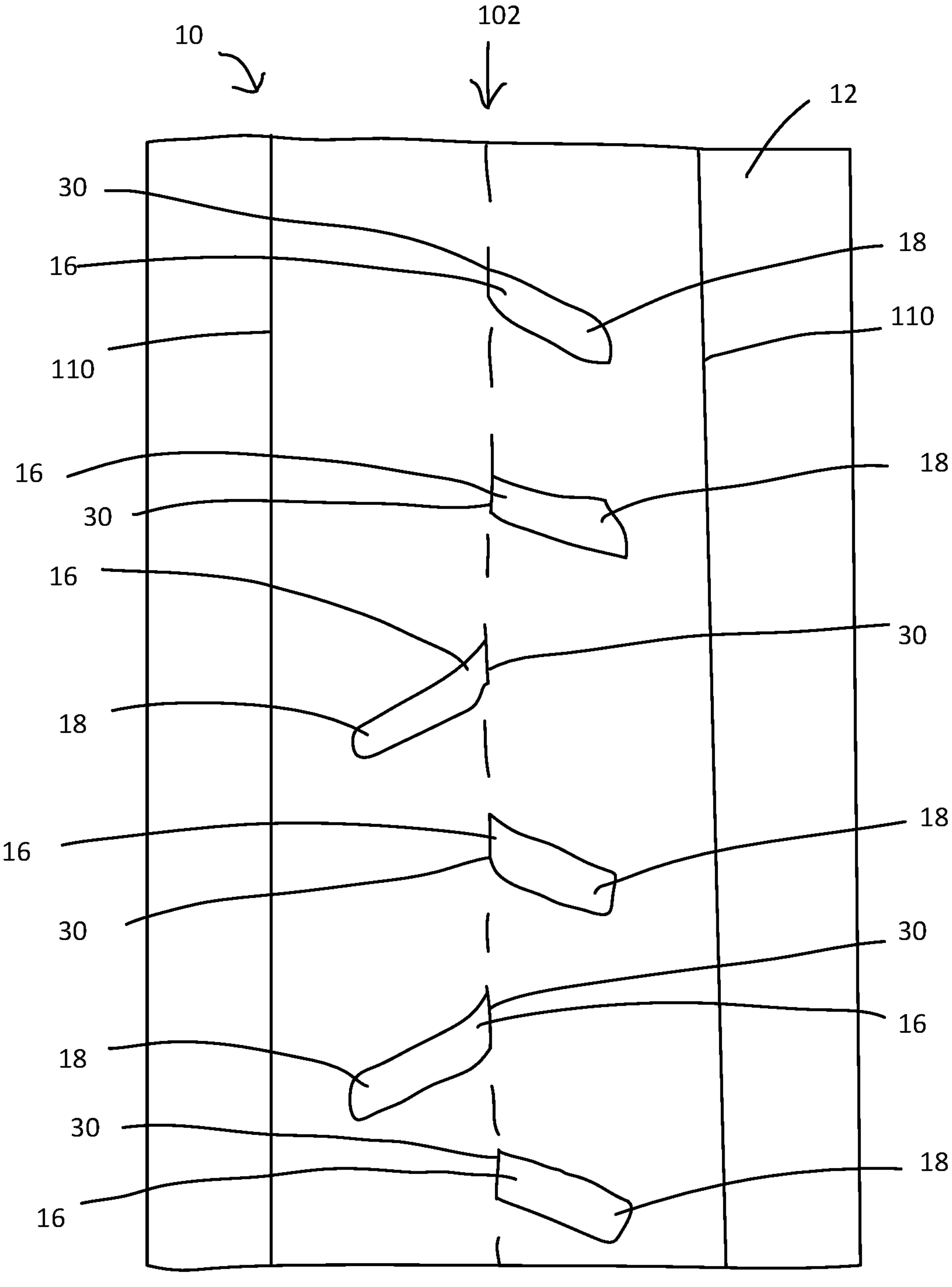
FIG. 22 shows another embodiment with six of the packing strip with residue lines.

FIG. 22 shows an embodiment with six of the packing strip 18 of the second portion 16. For comparison, assume that the substantially linear orientation of the packing strip 18 of the WCD 10 shown in FIG. 23 and the substantially linear orientation of the packing strip 18 of the WCD 10 shown in FIG. 24 are substantially the same length. In this comparison of configurations, therefore the embodiment shown in FIG. 24 would have twice as many of the packing strip 18 as the embodiment shown in FIG. 23. Because of this increased density of the packing strip 18 found in the embodiment of FIG. 24, a curvature of the residue line 110 seen in FIG. 23 may be substantially absent. In other words, the increased density of the packing strip 18 found in the embodiment of FIG. 24 wicks the fluid, bodily waste, or infectious material into the first portion 12 to leave the residue line that is approximately linear. Of course, the second portion 16 shown as in FIG. 24 may be of any type of the second portion 16 and packing strip 18 disclosed in the present application. How far the fluid and other materials flow into the first portion 12 will, of course, depend on the viscosity of the fluid, type of material present, etc. that has been wicked.

Figure 23:
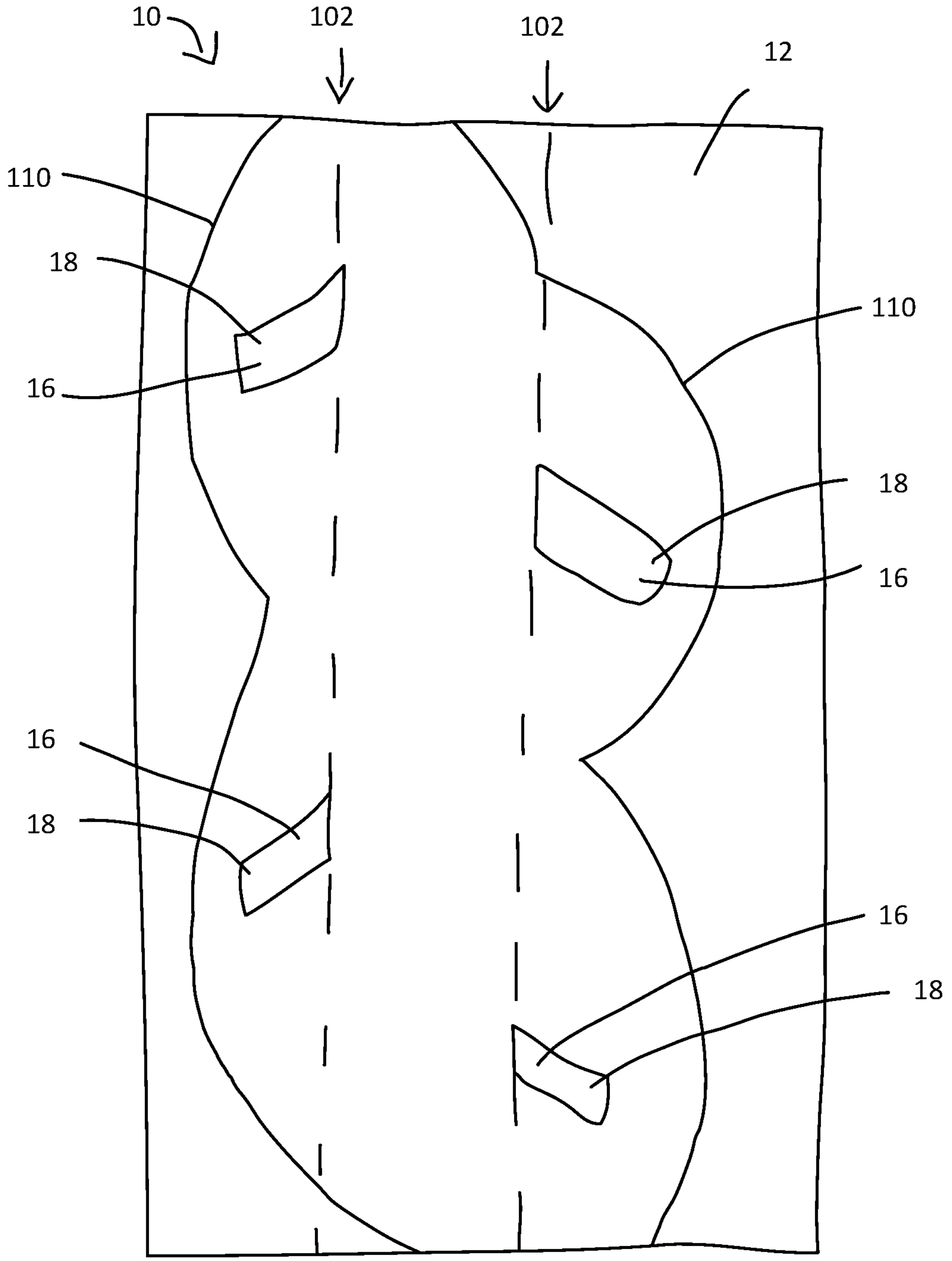
FIG. 23 shows another embodiment in which each of the packing strip are not all in a single substantially linear orientation.
Figure 24:
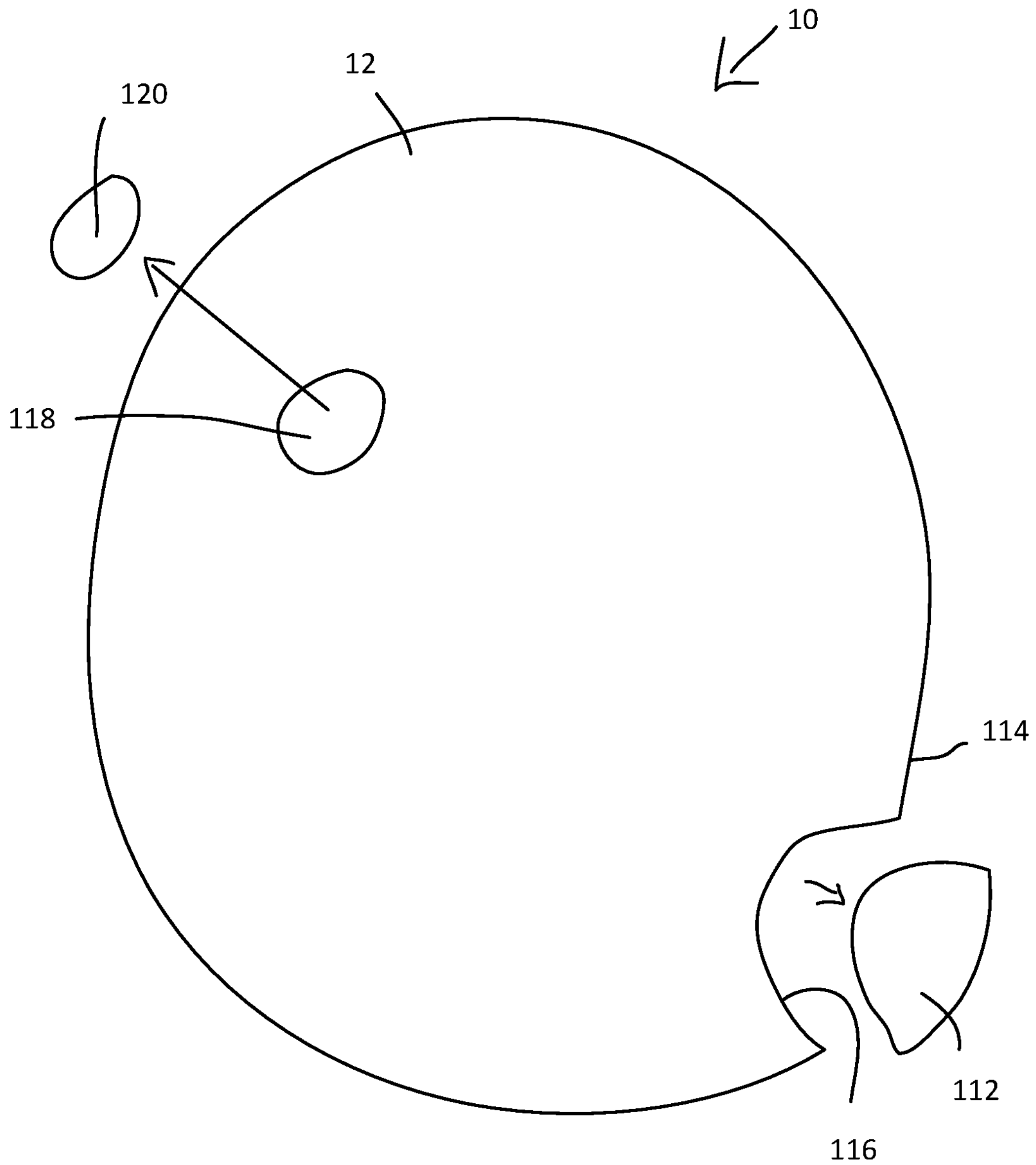
FIG. 24 shows a top view of another embodiment of the wound care device to accommodate surrounding items or obstructions at the skin surface.

FIG. 23 shows an embodiment in which the packing strip 18 of the second portion 16 are not all on one of the substantially linear orientation 102. Any suitable configuration or orientation of one or more of the packing strip 18 on the first portion 12 is contemplated. By not manufacturing all of the packing strip 18 in the WCD 10 in one of the substantially linear orientation 102, the WCD 10 may be able to use more of the first portion 12 for absorption of the fluid and other materials, and that may increase absorbency of the WCD 10 overall by making more use of the first portion 12 overall. Again, not all the packing strip 18 needs to be in the body of the patient, some of the packing strip 18 may remain outside the body. Of course, the second portion 16 shown as in FIG. 24 may be of any type of the second portion 16 and packing strip 18 disclosed in the present application. How far the fluid and other materials flow into the first portion 12 will, of course, depend on the viscosity of the fluid, type of material present, etc. that has been wicked.

Figure 26:
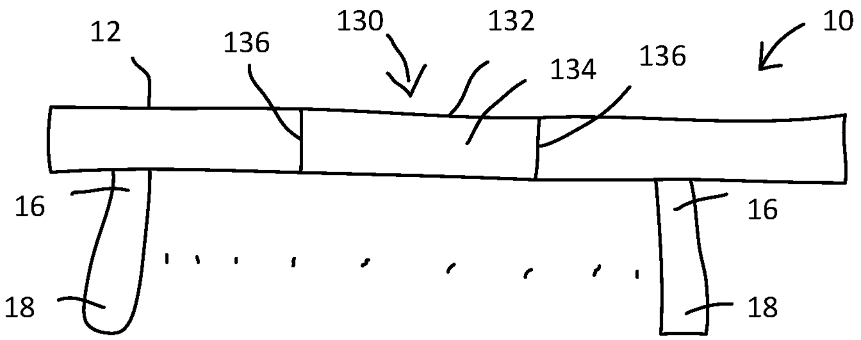
FIG. 26 shows another embodiment of the wound care device with an integrated medicament.

FIG. 24 shows another embodiment of the WCD 10 to accommodate surrounding items or obstructions at the skin surface that would prevent the first portion 12 from making good contact with the skin surface. FIG. 26 depicts a top view of this additional embodiment of the WCD 10 whose first portion 12 may optionally include a removed portion 112 removed from an edge 114 of the first portion 12 to form a recess 116. For example, when a patient has a stoma having a tube or other lumen that is coupled thereto and the WCD 10 needs to be used close that stoma/tube, the WCD 10 can be positioned as described previously and the first portion 12 can be positioned such that the recess 116 may be positioned closely adjacent the stoma/tube, thereby allowing the first portion 12 of the WCD 10 to make good contact with the skin surface and not be interfere with by the stoma/tube. It should be further understood that the shape of the recess 116 is by way of example only and it is not limited to a semi-circular contour but may optionally include any shape and size. In addition, the relative position of the recess 116 can be located along any portion of the edge 114 of the first portion 12.

Optionally, an interior portion away from the edge 114 of the first portion 12 may form an opening 118 of the first portion 12 when a removed portion 120 is removed from the first portion 12. Thus, where the incision or wound is located at a position closely adjacent some obstruction (e.g., a stoma, a tube, a medical device, etc.) that would prevent the first portion 12 from making sufficient contact with the skin surface, the obstruction (not shown) can be passed through the opening 118 to permit the first portion 12 to be positioned flush against the skin surface. Again, the opening 118 is shown by way of example only; other shapes and other locations on the first portion 12 may optionally include the opening 118, and the opening 118 may be of any suitable size and shape.

Figure 25:
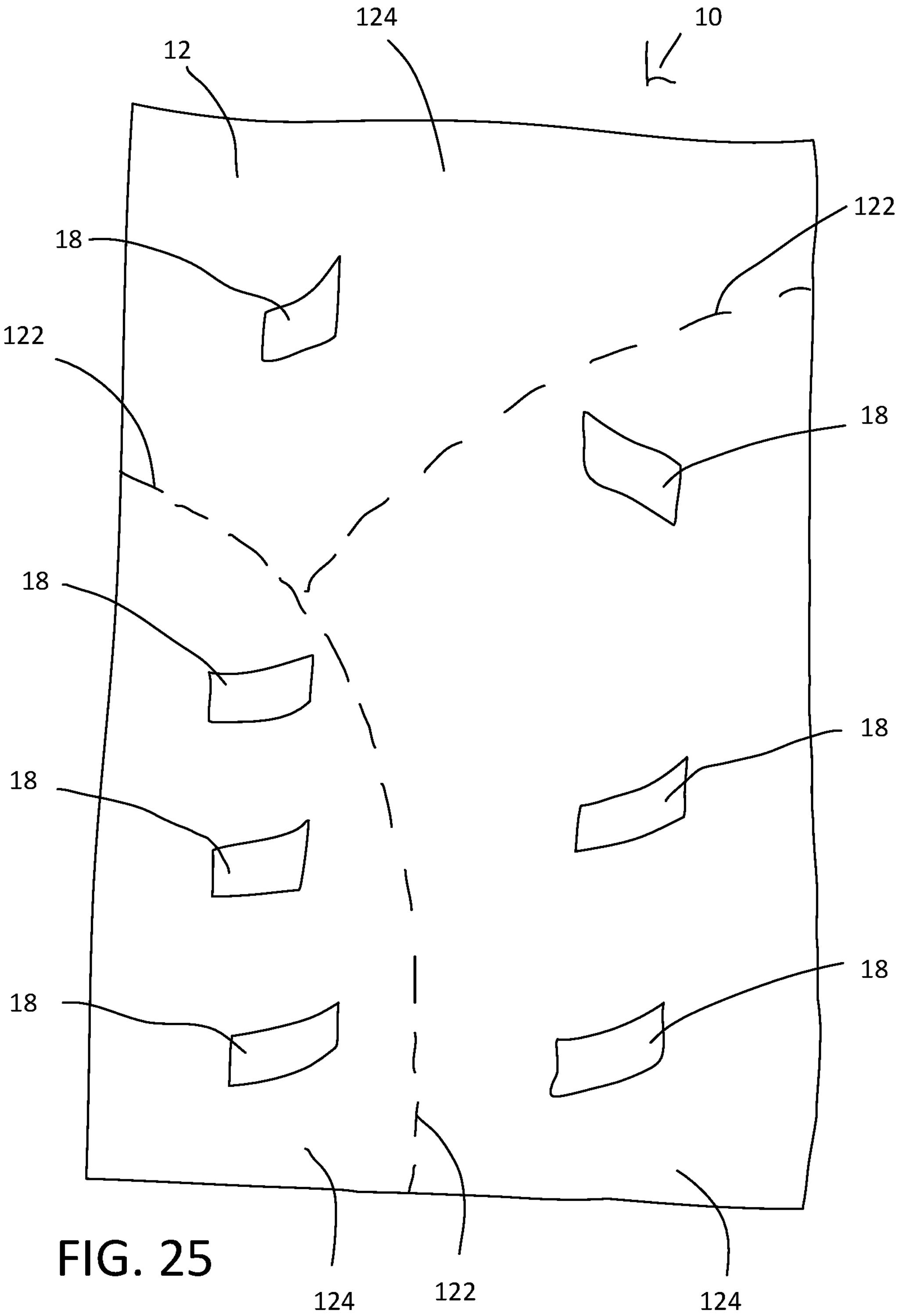
FIG. 25 shows another embodiment of the wound care device that reinforces that the wound care device may be of any suitable size and shape.

FIG. 25 shows another embodiment of the WCD 10 that reinforces, as mentioned earlier, that WCD 10 may be of any suitable size and shape of the first portion 12. There may one or more the packing strip 18. In addition, WCD 10 may be constructed in such a manner that the surgeon at the time of application of WCD 10 to the patient may find it convenient to adapt the WCD 10 to the wound. By manufacturing the WCD 10 with any suitable shape and size with easily separated, such as with a perforation line 122, into two of more of a first sub-portion 124 such as by tearing along one or more of the perforation line 122, the surgeon may be able to throw away an unneeded pieces of the first sub-portion 124 of the WCD 10 or use the separated piece of the first sub-portion 124 in a new orientation with respect to each of the other of the first sub-portion 124.

FIG. 26 shows another embodiment of the WCD 10 with an integrated medication delivery system 130. Optionally, the integrated medication delivery system 130 may include a medicament reservoir 132 configured to contain a medicament 134. The medicament 134 is a substance used for medical treatment. When the medicament 134 is in the medicament reservoir 132, the medicament 134 may not be in fluid communication with the second portion 16 or the packing strip 18 of the second portion 16. Optionally one or more of a divider 136 of the integrated medication delivery system 130 may be present to prevent the medicament 134 in the medicament reservoir 132 from being in fluid communication with the second portion 16, the packing strip 18, or both. The integrated medication delivery system 130 may positioned as part of the first portion 12 as show, or as port of the second portion 16, as not shown.

Figure 27:
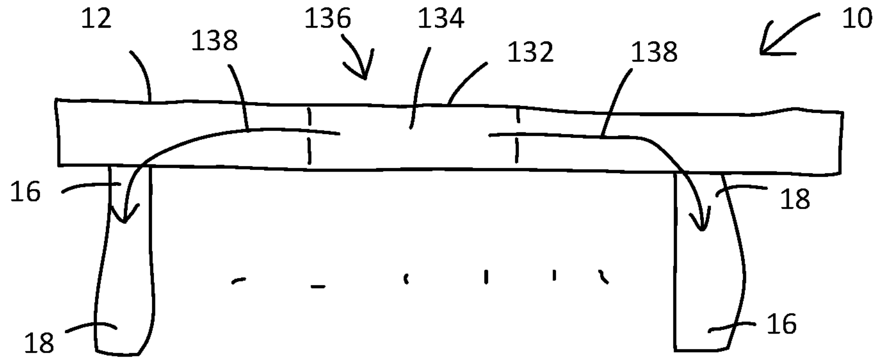
FIG. 27 shows another embodiment of the wound care device in which the storage area of the medicament is ruptured.

FIG. 27 shows an embodiment of the WCD 10 with the integrated medication delivery system 130. Optionally, the integrated medication delivery system 130 may include the medicament reservoir 132 configured to contain the medicament 134. The medicament 134 is a substance used for medical treatment. When the medicament 134 is in the medicament reservoir 132, the medicament 134 may not be in fluid communication with the second portion 16 or the packing strip 18 of the second portion 16. Optionally one or more of the divider 136 of the integrated medication delivery system 130 may be present to prevent the medicament 134 in the medicament reservoir 132 from being in fluid communication with the second portion 16, the packing strip 18, or both. Optionally, the one or more of the divider 136 of the may be friable, such that the one or more of the divider 136 may be easily crumbled or pulverized when the WCD 10 is used on the patient. The surgeon may apply pressure to the integrated medication delivery system 130 to rupture one of more of the divider 136 so that the medicament 134 is released in direction of an arrow 138 from the medicament reservoir 132, and the medicament is then in fluid communication with the second portion, the packing strip 18, or both. Thus, the surgeon may be able to provide local application of the medicament to the wound of the patient. The integrated medication delivery system 130 may positioned as part of the first portion 12 as show, or as port of the second portion 16, as not shown.

Figure 28:
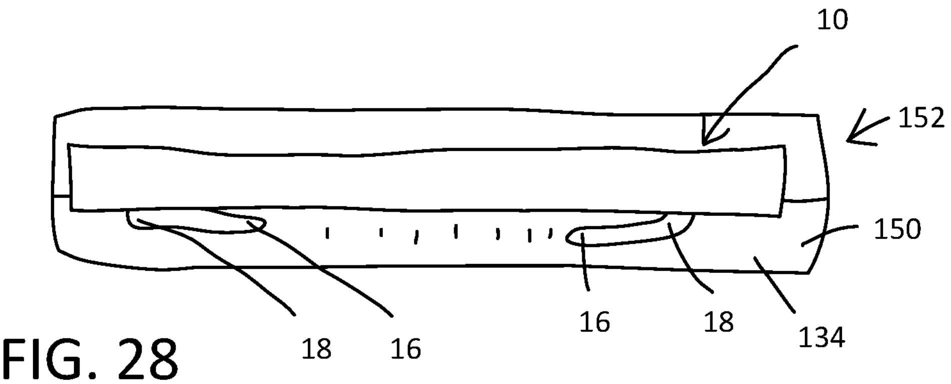
FIG. 28 shows another embodiment of the wound care device in which the medicament is in a container where the second portion is soaked in the medicament.

FIG. 28 shows another embodiment of the WCD 10 in which the medicament 134 is stored in a holding area 150. Optionally, the integrated medication delivery system 130 may include the medicament reservoir 132 configured to contain the medicament 134. The medicament 134 is a substance used for medical treatment. The medicament 134 is in fluid communication with the second portion 16, the packing strip 18, or both when the WCD 10 in storage prior to use. In this situation, the second portion 16, the packing strip 18, or both would be soaked with the medicament 134. The medicament is ready for use when the WCD 10 is removed from a storage container 152. Thus, the surgeon may be able to provide local application of the medicament to the wound of the patient. The integrated medication delivery system 130 may positioned as part of the first portion 12 as shown, or as part of the second portion 16 as not shown.

Of course, the second portion 16, the packing strip 18, or both the second portion 16 and the packing strip 18 of the WCD 10 could be soaked in the medicament 134 before or after the WCD 10 is stored in the storage container 152.

Figure 29:
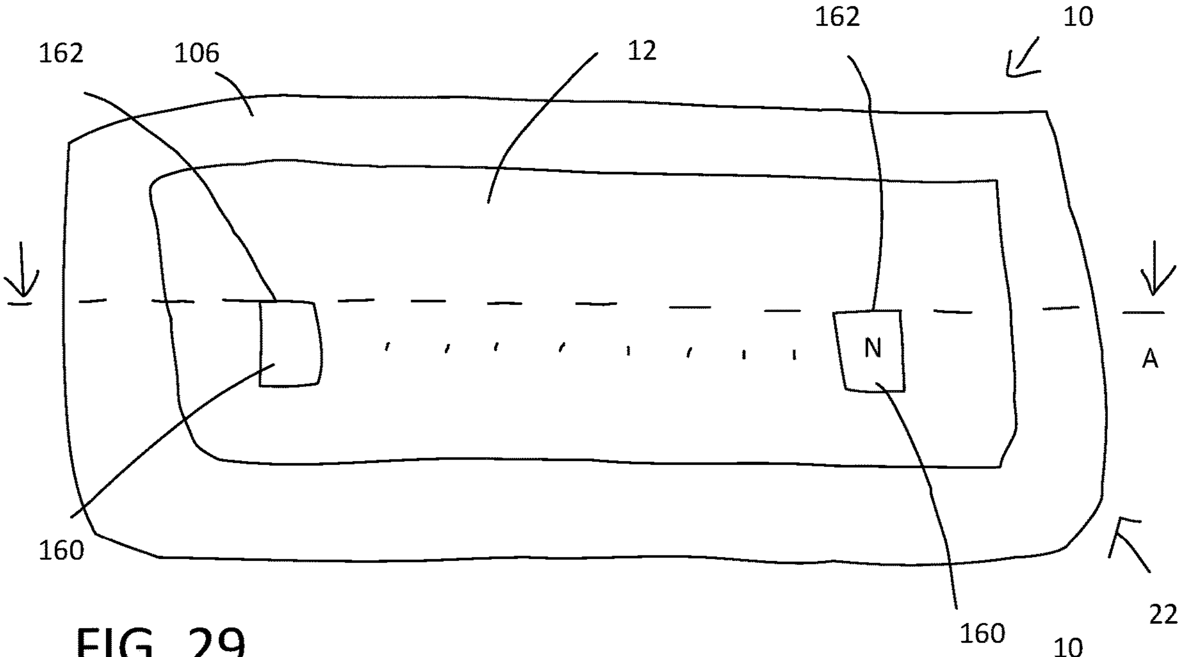
FIG. 29 shows in top view of another embodiment of the wound care device in which an indicator is visible.

The medicament 134 may be antimicrobial (antibiotic, antiviral, etc.), pain medication, Nonsteroidal anti-inflammatory drugs (NSAIDs), Corticosteroids, Opioids, Muscle relaxants, Anti-anxiety drugs, antidepressants, anticonvulsant, Local anesthetics (such as Ketamine, Marcaine, and lidocaine). It should be noted that although not required, an anti-microbial composition may be applied to either the first portion 12, the second portion 16, or both. Similarly, pain medications or any other of the medicament 134 may be applied to either the first portion 12, the second portion 16, or both FIG. 29 shows in top view of another embodiment of the WCD 10 in which an indicator 160 is visible. The indicator 160 may be configured to monitor the wound to detect status and information, such as temperature, pH (such as pH below 7 to indicate patient is acidotic), etc. For example, the indicator 160 could be a single use sterile thermometer, with the exemplary technology including 3M Tempa DOT Clinical Disposable Thermometers that are disposable and for single use. As another example, the indicator 160 could be a single use sterile pH monitor, with exemplary technology including Johnson test paper pH Strips for Hospital Use. The indicator 160 could appear on top of the first portion 12. The adhesive border 106 may be used to releasably connect the WCD 10 to the skin 22. The indicator 160 may be visible through transparency of a window 162 that may be present on top of the first portion 12. Optionally, a transparent surface may extend across the top of the first portion 12 that extends to the adhesive border 106. There may be 1 to N number of the indicator 160. The indicator 160 is shown in orientation essentially perpendicular to the wound on which the WCD 10 will be used, however other orientations are contemplated.

Figure 29A:
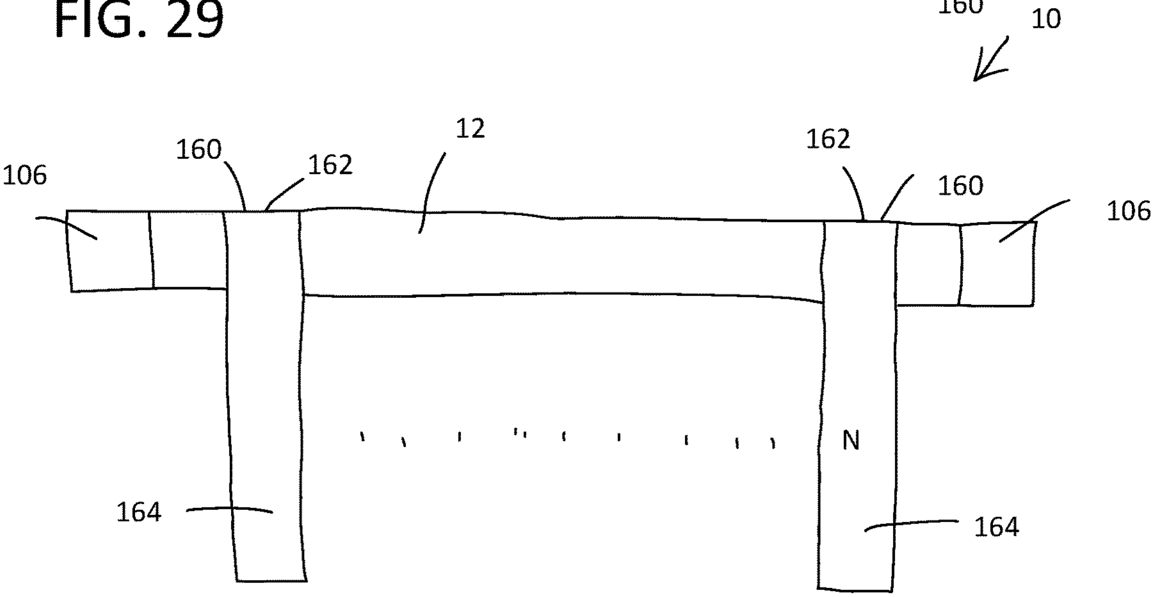
FIG. 29A shows in cross-section view the embodiment of the wound care device in FIG. 29 in which an indicator is visible.

FIG. 29A shows in cross-section view the embodiment of the WCD 10 in FIG. 29 in which the indicator 160 is visible through the window 162 on top of the first portion 12. The adhesive border 106 surrounding the first portion 12 is shown. The indicator 160 may be operatively coupled to a testing strip 164 that may be configured to be placed in the wound. The indicator 160 may be configured to monitor the wound to detect status and information, such as temperature, pH, etc. There may be 1 to N number of the indicator 160.

Figure 30:
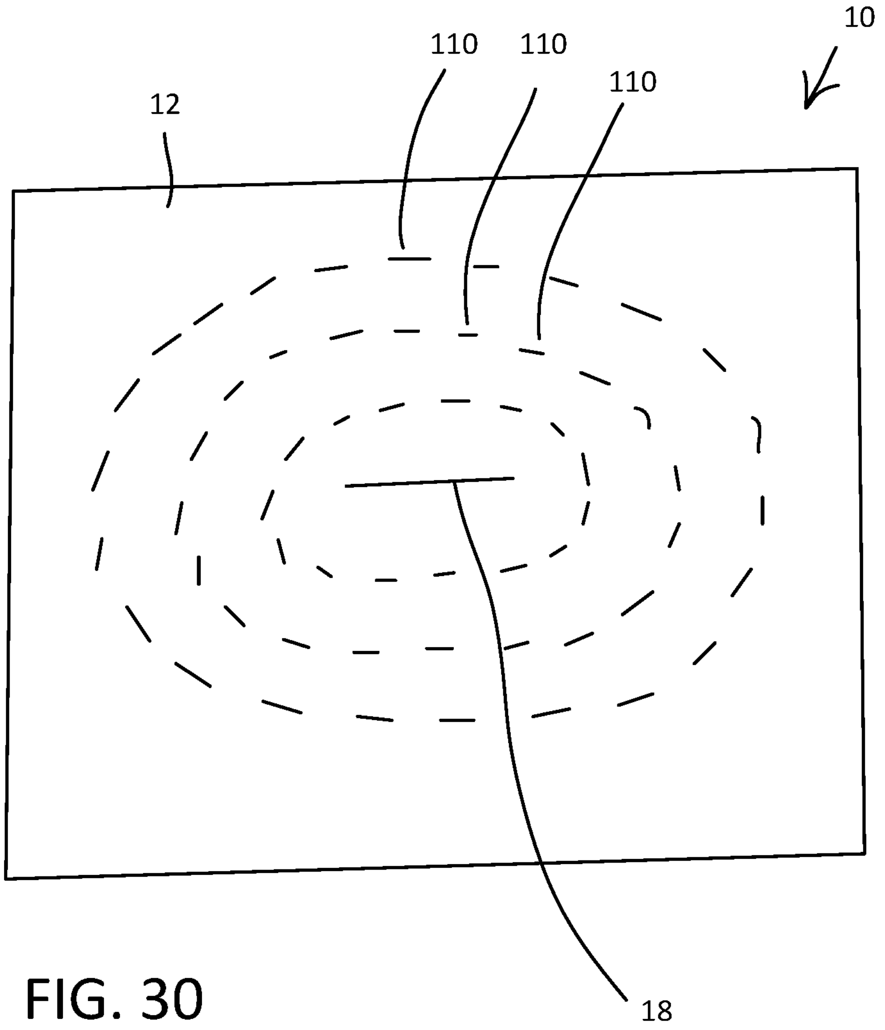
FIG. 30 shows another embodiment of the wound care device in which a residue line on successive days is visible.

FIG. 30 shows another embodiment of the WCD 10 in which a residue line on successive days is visible. Over time, the wicking strip 18 will wick more fluid and other materials from the wound. Each use of the WCD 10 in the wound may have a unique exhortation pattern of the fluid and other materials, however broadly speaking one would expect more fluid and other materials to be absorbed over time. As such, there may be a series of the residue line extending on the first portion 12 that expands outward from the wicking strip 18 over time. This pattern of the residue line 110 extending over time may be seen on a bottom of the first portion 12, as shown. Interestingly, a similar pattern of the residue line 110 extending over time may be seen on a top of the first portion 12 when a window, such as a transparent cover, is over the top of the first portion 12. The window may be similar or separate from the window 162 discussed regarding FIGS. 29 and 29A.

By providing visibility of the indicator 160 and the residue line 110, there may be a variety of monitoring possibilities available. In addition to hospital use, the WCD 10 may be used in an outpatient setting, home setting, or other settings where wound care is performed. The information in the indicator 160 and the residue 110 may be shared with the surgeon by photo, video, verbal report, etc. The information may be entered into the electronic health record, sent by secured email, sent by secured text, etc. based on this information, the surgeon may elect to have the patient seen sooner due to increased temperature, acidity with decreased pH, etc. The WCD 10 may be changed sooner than originally planned based on the absorption pattern seen based on the residue line 110. Other possibilities are contemplated.

Figure 31:
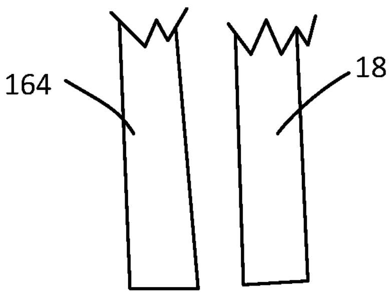
FIG. 31 shows in side view an embodiment of the packing strip and the testing strip.

FIG. 31 shows in side view an embodiment of the packing strip 18 and the testing strip 164 in which the packing strip 18 and the testing strip 164 may be of substantially the same length and so the packing strip 18 and the testing strip 164 may be configured to go to the approximately the same depth of the wound when placed in the same one of the closure device interspace 42 (see FIG. 5). While the packing strip 18 and the testing strip 164 may be contactingly adjacent in the wound, the packing strip 18 and the testing strip 164 may not be contactingly adjacent outside of the wound.

Figure 32:
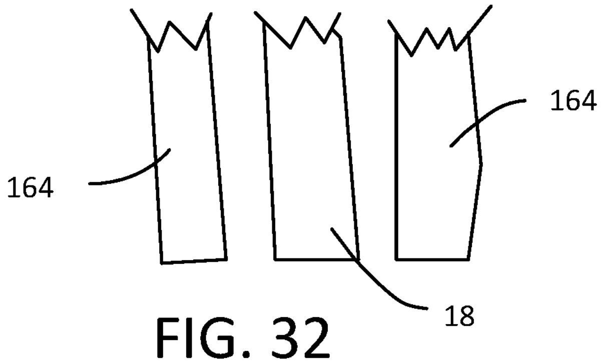
FIG. 32 shows in side view another embodiment of the packing strip and the testing strip.

FIG. 32 shows in side view another embodiment of the packing strip 18 and two of the testing strip 164 in which the packing strip 18 is positioned between a pair of the testing strip 164. The packing strip 18 and the two of the testing strip 164 may be of substantially the same length and so the packing strip 18 and the two of the testing strip 164 may be configured to go to approximately the same depth of the wound when placed in the same one of the closure device interspace 42 (see FIG. 5). While the packing strip 18 and the two of the testing strip 164 may be contactingly adjacent in the wound, the packing strip 18 and the two of the testing strip 164 may not be contactingly adjacent outside of the wound.

Figure 33:
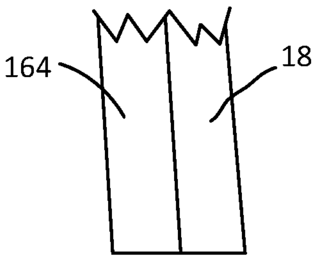
FIG. 33 shows in side view another embodiment of the packing strip and the testing strip.

FIG. 33 shows in side view another embodiment of the packing strip 18 and the testing strip 164 in which the packing strip 18 and the testing strip 164 may be of substantially the same length and so the packing strip 18 and the testing strip 164 may be configured to go to the approximately the same depth of the wound when placed in the same one of the closure device interspace 42 (see FIG. 5). The packing strip 18 and the testing strip 164 may be configured to be contactingly adjacent, which may be achieved through adhesive, welding, stitching, or other fastener. The packing strip 18 and the testing strip 164 may therefore provide support and strength to maintain structural integrity of the packing strip 18 and the testing strip 164.

Figure 34:
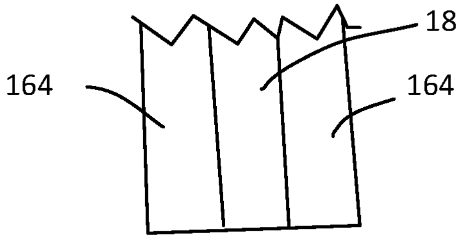
FIG. 34 shows in side view another embodiment of the packing strip and the testing strip.

FIG. 34 shows in side view another embodiment of the packing strip 18 and N number of the testing strip in which the packing strip 18 is positioned between a pair of the testing strip 164. The packing strip 18 and the two of the testing strip 164 may be of substantially the same length and so the packing strip 18 and the two of the testing strip 164 may be configured to go to approximately the same depth of the wound when placed in the same one of the closure device interspace 42 (see FIG. 5). The packing strip 18 and the two of the testing strip 164 may be configured to be contactingly adjacent, which may be achieved through adhesive, welding, stitching, or other fastener. The packing strip 18 and the two of the testing strip 164 may therefore provide support and strength to maintain structural integrity of the packing strip 18 and the two of the testing strip 164.

Figure 35:
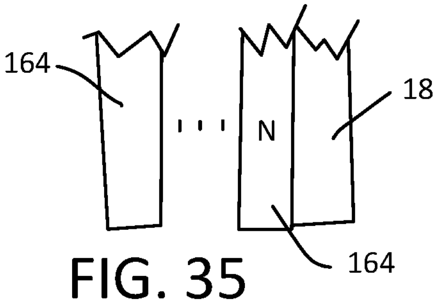
FIG. 35 shows in side view another embodiment of the packing strip and the testing strip.

FIG. 35 shows in side view another embodiment of the packing strip 18 and N number of the testing strip in which the packing strip 18 and the N number of the testing strip 164 may be of substantially the same length and so the packing strip 18 and the N number of the testing strip 164 may be configured to go to the approximately the same depth of the wound when placed in the same one of the closure device interspace 42 (see FIG. 5). The packing strip 18 and at least one of the N number of the testing strip 164 may be configured to be contactingly adjacent, which may be achieved through adhesive, welding, stitching, or other fastener. Each of the N number of the testing strip 164 may or may not be configured to be contactingly adjacent to the testing strip 164 that is adjacent.

Figure 36:
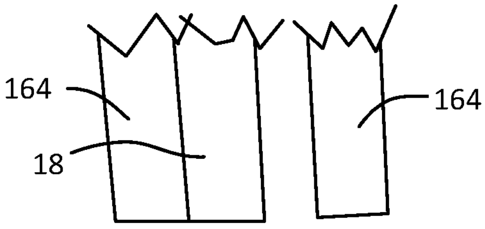
FIG. 36 shows in side view another embodiment of the packing strip and the testing strip.

FIG. 36 shows in side view another embodiment of the packing strip 18 and two of the testing strip 164 in which the packing strip 18 is positioned between a pair of the testing strip 164. The packing strip 18 and the two of the testing strip 164 may be of substantially the same length and so the packing strip 18 and the two of the testing strip 164 may be configured to go to approximately the same depth of the wound when placed in the same one of the closure device interspace 42 (see FIG. 5). While the packing strip 18 and the two of the testing strip 164 may be contactingly adjacent in the wound, the packing strip 18 and a first of the two of the testing strip 164 may not be contactingly adjacent outside of the wound. On the other hand, The packing strip 18 and a second oth the testing strip 164 may be configured to be contactingly adjacent, which may be achieved through adhesive, welding, stitching, or other fastener.

Figure 37:
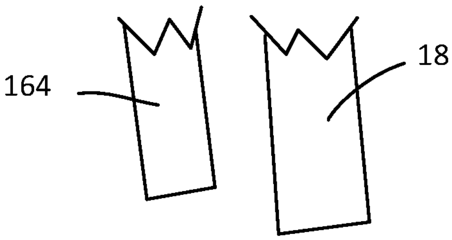
FIG. 37 shows in side view another embodiment of the packing strip and the testing strip.

FIG. 37 shows in side view another embodiment of the packing strip 18 and the testing strip 164 in which the packing strip 18 and the N number of the testing strip 164 may be of substantially a different length and so the packing strip 18 and the testing strip 164 may be configured to go to a substantially different depth of the wound when placed in the same one of the closure device interspace 42 (see FIG. 5). In this configuration, the packing strip 18 may be longer than the testing strip 164, so the packing strip 18 may go to a greater depth of the wound.

Figure 38:
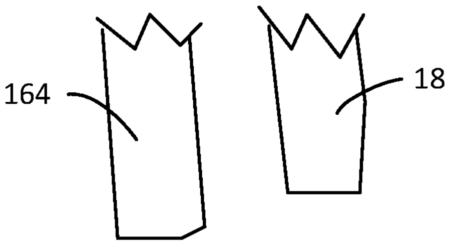
FIG. 38 shows in side view another embodiment of the packing strip and the testing strip.

FIG. 38 shows in side view another embodiment of the packing strip 18 and the testing strip in which the packing strip 18 and the N number of the testing strip 164 may be of substantially a different length and so the packing strip 18 and the testing strip 164 may be configured to go to a substantially different depth of the wound when placed in the same one of the closure device interspace 42 (see FIG. 5). In this configuration, the packing strip 18 may be shorter than the testing strip 164, so the packing strip 18 may go to a lesser depth of the wound.

Figure 40:
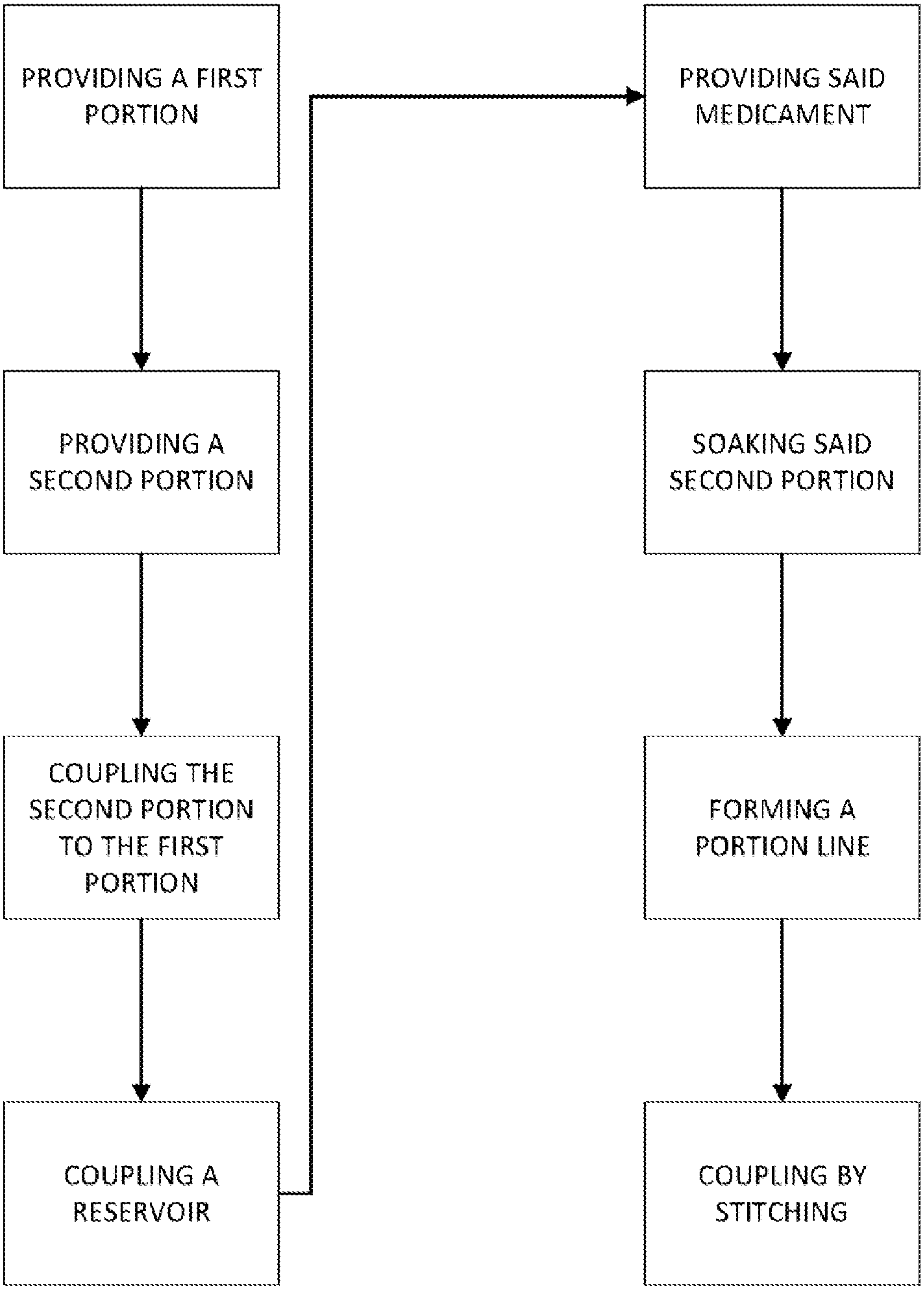
FIG. 40 provides a flow chart for a method of manufacturing the wound care device via routine 200 illustrative of various steps that may be carried out to manufacture the wound care device.

FIG. 40 provides a flow chart for a method of manufacturing the WCD 10 via routine 200 illustrative of various steps that may be carried out to manufacture the WCD 10 of the foregoing discussion.

At step 202, the first portion may be provided. The first portion may include a first fluid absorbent material having a first fluid-absorbing characteristic.

At step 204, the second portion may be provided. The second portion may include a second fluid absorbent material having a second fluid-absorbing characteristic that may be different from the first fluid-absorbing characteristic. The second portion may have a proximal end and a distal end.

At step 206, the second portion may be coupled to a central portion of the first portion such that the proximal end of the second portion may be in fluid communication with said first portion At step 208, the reservoir may be coupled to the first portion. Alternatively, the reservoir may be coupled to the second portion. Optionally, the reservoir may be coupled to the first portion and the second portion.

At step 210, optionally, said medicament may be provided to said reservoir.

At step 212, optionally, said second portion may be soaked in said medicament.

At step 214, optionally, the perforation line may be formed in part of the wound care device.

At step 216, optionally, the second portion may be coupled to the central portion by stitching.

Optionally, all the embodiments disclosed can be interconnected with each other in one of the WCD 10. It is possible have multiple different types of the packing strip 18, the testing strip 164, etc. inserted into the wound 14. Of course, the surgeon may use one or more of the WCD 10 with the wound 14.

The physical construction of the packing strip 18 may optionally vary and can be referred to using any number of terms, such as but not limited to, strip, loop, tab, cord, appendage, tentacle, finger, etc. When the WCD 10 is used, all of the packing strip 18 do not need to be inserted into the wound of the patient.

Thus, the present disclosure relates to an apparatus/method of wound infection prevention and healing acceleration and life. The WCD 10 provides the effective post-surgical clean contaminated, contaminated, clean and infected incision when the rate of infection potential is considered significant. The apparatus/method may also be used in a variety of medical surgeries interventions and procedures. The WCD 10 can also be used in veterinary medicine or dental medicine.

The apparatus and method for wound care device (WCD) 10 is useful for preventing SSI infection for the following surgeries including but is not limited to: general surgery procedures, colorectal, OBGYN procedures, urology, vascular surgeries, and neurosurgery procedures. The incisions or wounds closed following their respective surgeries are susceptible to high infection rates and slow patient recovery periods which also impact the physician, staff, hospital, insurer, etc. Moreover, SSI costs hospitals billions of dollars every year in the U.S. and insurance companies do not reimburse hospitals for maladies caused by infection, and corresponding complications, due to surgical site infection.

It should be further understood that the term WCD includes any all of kinds of kits that comprise the WCD and any associated components (e.g., a plurality of WCDs; tools that may be used by the surgeon to insert the second portion 16 into wound site (e.g., pliers, tweezers, dissectors, etc.) that are provided with the WCD 10 itself.

Thus, the apparatus and method for the wound care device (WCD) 10 accelerates the healing process by reducing the healing time by an average of 2 days per patient, which among other things, reduces hospital stay periods.

While the disclosure has been described in detail and with reference to specific examples thereof, it will be apparent to one skilled in the art that various changes and modifications can be made therein without departing from the spirit and scope thereof.

What is claimed is:

1. A wound care device comprising:

a first portion that is configured to be applied over and external to a wound, said first portion comprising a first fluid absorbent material;

a second portion comprising a second fluid absorbent material, and having a proximal end and a distal end, wherein the proximal end is in fluid communication with said first portion, and wherein the distal end is configured to be positioned within the wound in a subcutaneous skin layer; and a reservoir operatively coupled to the first portion, wherein the reservoir is configured to contain a medicament;

wherein said first portion comprises a central portion to which said proximal end of said second portion is coupled, and wherein said first portion is adapted to form a cover over the wound when said distal end of said second portion is positioned within the wound;

wherein the first fluid absorbent material has a first fluid-absorbing characteristic and the second fluid absorbent material has a second fluid-absorbing characteristic different from the first fluid-absorbing characteristic; and wherein the first and second fluid absorbent materials are configured to wick liquids from the second portion to the first portion to facilitate removal of fluid and potentially infectious materials from the subcutaneous skin layer; wherein the reservoir is configured to come into fluid communication with the second portion when a wall of the reservoir is ruptured.

2. The wound care device of claim 1, wherein said wall is configured to act as a divider to thereby prevent said medicament from being in fluid communication with said second portion prior to being ruptured.

3. The wound care device of claim 2, wherein said divider is configured to be crumbled or pulverized to provide fluid communication between the reservoir and the second portion.

4. The wound care device of claim 1, further comprising an indicator configured to monitor the wound to thereby detect information relating to the wound.

5. The wound care device of claim 4, wherein the indicator is configured to detect temperature.

6. The wound care device of claim 4, wherein the indicator is configured to detect pH.

7. The wound care device of claim 4, wherein the indicator is provided on the first portion.

8. The wound care device of claim 4, wherein the indicator is operatively coupled to a testing strip configured to be placed in the wound.

9. The wound care device of claim 1, further comprising a transparent window configured to allow a residue line to be seen therethrough.

10. The wound care device of claim 1, wherein the first material comprises an x-ray detectable material.

11. The wound care device of claim 1, wherein the second material comprises an x-ray detectable material.

12. The wound care device of claim 10 or 11, wherein the x-ray detectable material includes one or more of blue x-ray detectable barium sulfate strands, white x-ray detectable barium sulfate strands, and tungsten filaments.

13. The wound care device of claim 1, comprising a perforation line, wherein the wound care device is configured to be torn along the perforation line to divide the wound care device into two or more sub-portions.

14. A method of manufacturing a wound care device, the method comprising:

providing a first portion comprising a first fluid absorbent material having a first fluid-absorbing characteristic;

providing a second portion comprising a second fluid absorbent material having a second fluid-absorbing characteristic that is different from the first fluid-absorbing characteristic, the second portion having a proximal end and a distal end, wherein the first and second fluid absorbent materials are configured to wick liquids from the second portion to the first portion to facilitate removal of fluid and potentially infectious materials from the subcutaneous skin layer;

coupling the second portion to a central portion of the first portion such that the proximal end of the second portion is in fluid communication with said first portion, wherein the second portion is coupled to the central portion by welding; and coupling a reservoir to the first portion.

* * * * *